US009737476B2

(12) United States Patent
Fournial et al.

(10) Patent No.: US 9,737,476 B2
(45) Date of Patent: Aug. 22, 2017

(54) COSMETIC USE OF AN ALBIZIA JULIBRISSIN EXTRACT AND CORRESPONDING TOPICAL COMPOSITION

(71) Applicant: Sederma, Le Perray en Yvelines (FR)

(72) Inventors: Arnaud Fournial, Paris (FR); Claire-Marie Grizaud, Uccle (BE); Philippe Mondon, Montrouge (FR)

(73) Assignee: Sederma (FR)

( * ) Notice: Subject to any disclaimer, the term of this patent is extended or adjusted under 35 U.S.C. 154(b) by 592 days.

(21) Appl. No.: 14/345,285

(22) PCT Filed: Sep. 27, 2012

(86) PCT No.: PCT/IB2012/055137
§ 371 (c)(1),
(2) Date: Mar. 17, 2014

(87) PCT Pub. No.: WO2013/046137
PCT Pub. Date: Apr. 4, 2013

(65) Prior Publication Data
US 2015/0017269 A1    Jan. 15, 2015

Related U.S. Application Data

(60) Provisional application No. 61/564,977, filed on Nov. 30, 2011.

(30) Foreign Application Priority Data

Sep. 27, 2011  (FR) ..................... 11/58598

(51) Int. Cl.
| A61K 8/97 | (2017.01) |
| A61Q 19/08 | (2006.01) |
| A61K 45/06 | (2006.01) |
| A61K 36/48 | (2006.01) |
| A61K 38/05 | (2006.01) |
| A61K 38/06 | (2006.01) |
| A61K 38/07 | (2006.01) |
| A61K 38/08 | (2006.01) |
| A61K 8/34 | (2006.01) |
| A61K 8/49 | (2006.01) |
| A61K 8/60 | (2006.01) |
| A61K 8/64 | (2006.01) |
| A61Q 19/00 | (2006.01) |
| A61Q 19/02 | (2006.01) |
| A61Q 19/06 | (2006.01) |

(52) U.S. Cl.
CPC ............ *A61K 8/97* (2013.01); *A61K 8/342* (2013.01); *A61K 8/498* (2013.01); *A61K 8/4926* (2013.01); *A61K 8/4986* (2013.01); *A61K 8/602* (2013.01); *A61K 8/64* (2013.01); *A61K 36/48* (2013.01); *A61K 38/05* (2013.01); *A61K 38/06* (2013.01); *A61K 38/07* (2013.01); *A61K 38/08* (2013.01); *A61K 45/06* (2013.01); *A61Q 19/00* (2013.01); *A61Q 19/02* (2013.01); *A61Q 19/06* (2013.01); *A61Q 19/08* (2013.01); *A61K 2800/522* (2013.01); *A61K 2800/72* (2013.01)

(58) Field of Classification Search
None
See application file for complete search history.

(56) References Cited

U.S. PATENT DOCUMENTS

| 7,090,872 B2 | 8/2006 | Nagamine et al. |
| 7,544,375 B1 | 6/2009 | Bellin et al. |
| 2006/0216251 A1 | 9/2006 | Morariu |
| 2009/0098223 A1 | 4/2009 | Nam |

FOREIGN PATENT DOCUMENTS

| FR | 2285142 A1 | 4/1976 |
| FR | 2801787 A1 | 6/2001 |
| JP | 2048515 | 8/1988 |
| JP | 2000143488 A | 5/2000 |
| JP | 4342519 B2 | 10/2009 |
| JP | 2009242296 A | 10/2009 |
| JP | 2010235548 A | 10/2010 |
| KR | 20020080657 A | 10/2002 |
| KR | 20100090530 A | 8/2010 |

OTHER PUBLICATIONS

Cho (KR 2010-0090530—English translation) Aug. 2010.*
Database WPI Week 201072 Thomson Scientific. London, GB; AN 2010-N33764 XP002678649, Jul. 3, 2012.
Lau et al: "Identification and quantification of glycoside flavonoids in the energy crop Albizia julibrissin", Bioresource Technology, Elsevier BV GB, vol. 98. No. 2, Jan. 1, 2007 (Jan. 1, 2007), pp. 429-435, XP005645236, ISSN: 0960-8524, DOI: 10.1016/J.BIORTECH.2005.12.011 Abstract; p. 429-p. 434.
Nehdi et al: "Characteristics. chemical composition and utilisation of Albizia julibrissin seed oil", Industrial Crops and Products. Elsevier, NL, vol. 33, No. 1, Jan. 1, 2011 (Jan. 1, 2011), pp. 30-34, XP027537414, ISSN: 0926-6690 [retrieved on Sep. 28, 2010] the whole document.

(Continued)

*Primary Examiner* — Susan Hoffman
(74) *Attorney, Agent, or Firm* — Lerner, David, Littenberg, Krumholz & Mentlik, LLP

(57) ABSTRACT

The present invention proposes an extract of *Albizia Julibrissin* for the cosmetic treatment of skin glycation. The extract is preferably obtained from flowers and/or seeds. Application to cosmetic formulations for treating cutaneous fatigue, in particular for improving the radiance of skin and eye contour (under eye bags and dark circles) and for treating the loss of skin suppleness. A preferred composition, particularly adapted for eye contour, comprises the *Albizia Julibrissin* extract combined with Darutoside that can be extracted from *Siegesbeckia Orientalis*.

9 Claims, 2 Drawing Sheets

(56) References Cited

OTHER PUBLICATIONS

Jae Hoon et al: "Darutoside, A Diterpenoid From Siegesbeckia Pubescens and Its Structure Revision Glc 3 OH H H", Jan. 1, 1979 (Jan. 1, 1979), pp. 894-895, XP055140451, Retrieved from the Internet: URL:http:jjwww.sciencedirect.comjscienceja rticlejpii/003194227980045X/
pdfft?md5=6567a97960ac5eeea798837a155ef201&pid=1-s2.0-00 3194227980045X-main.pdf [retrieved on Sep. 16, 2014] the whole document.
International Search Report and Written Opinion for Application No. PCT/IB2012/055137 dated Sep. 9, 2014.

* cited by examiner

Table 19. Reduction in facial fatigue during applications of the cream according to the invention (20 volunteers)

Time (in days)

Table 20. Reduction in facial fatigue during applications of the cream according to the invention (20 volunteers)

SEQUENCE LISTING

```
<160> NUMBER OF SEQ ID NOS: 10

<210> SEQ ID NO 1
<211> LENGTH: 6
<212> TYPE: PRT
<213> ORGANISM: artificial sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: amidation by a Palmitoyl chain on the N
      terminal end

<400> SEQUENCE: 1

Val Gly Val Ala Pro Gly
1               5

<210> SEQ ID NO 2
<211> LENGTH: 5
<212> TYPE: PRT
<213> ORGANISM: artificial sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: amidation by a Palmitoyl chain on the N
      terminal end
```

```
<400> SEQUENCE: 2

Lys Thr Thr Lys Ser
1               5

<210> SEQ ID NO 3
<211> LENGTH: 4
<212> TYPE: PRT
<213> ORGANISM: artificial sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: amidation by a Palmitoyl chain on the N
      terminal end

<400> SEQUENCE: 3

Gly Gln Pro Arg
1

<210> SEQ ID NO 4
<211> LENGTH: 5
<212> TYPE: PRT
<213> ORGANISM: artificial sequence
<220> FEATURE:
<223> OTHER INFORMATION: synthetic peptide

<400> SEQUENCE: 4

Lys Thr Thr Lys Ser
1               5

<210> SEQ ID NO 5
<211> LENGTH: 4
<212> TYPE: PRT
<213> ORGANISM: artificial sequence
<220> FEATURE:
<223> OTHER INFORMATION: synthetic peptide

<400> SEQUENCE: 5

Arg Ser Arg Lys
1

<210> SEQ ID NO 6
<211> LENGTH: 4
<212> TYPE: PRT
<213> ORGANISM: artificial sequence
<220> FEATURE:
<223> OTHER INFORMATION: synthetic peptide

<400> SEQUENCE: 6

Gly Gln Pro Arg
1

<210> SEQ ID NO 7
<211> LENGTH: 4
<212> TYPE: PRT
<213> ORGANISM: artificial sequence
<220> FEATURE:
<223> OTHER INFORMATION: synthetic peptide

<400> SEQUENCE: 7

Lys Thr Phe Lys
1

<210> SEQ ID NO 8
<211> LENGTH: 6
```

```
<212> TYPE: PRT
<213> ORGANISM: artificial sequence
<220> FEATURE:
<223> OTHER INFORMATION: Synthetic peptide

<400> SEQUENCE: 8

Gly Lys Thr Thr Lys Ser
1               5

<210> SEQ ID NO 9
<211> LENGTH: 6
<212> TYPE: PRT
<213> ORGANISM: artificial sequence
<220> FEATURE:
<223> OTHER INFORMATION: synthetic peptide

<400> SEQUENCE: 9

Val Gly Val Ala Pro Gly
1               5

<210> SEQ ID NO 10
<211> LENGTH: 5
<212> TYPE: PRT
<213> ORGANISM: artificial sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: amidation by a Palmitoyl chain on the N
      terminal end
<220> FEATURE:
<221> NAME/KEY: MISC_FEATURE
<222> LOCATION: (5)..(5)
<223> OTHER INFORMATION: Xaa being either a Methionine M or a Leucine L.

<400> SEQUENCE: 10

Tyr Gly Gly Phe Xaa
1               5
```

COSMETIC USE OF AN ALBIZIA JULIBRISSIN EXTRACT AND CORRESPONDING TOPICAL COMPOSITION

CROSS-REFERENCE TO RELATED APPLICATIONS

The present application is a national phase entry under 35 U.S.C. §371 of International Application No. PCT/IB2012/055137 filed Sep. 27, 2012, published in English, which claims priority from French Application No. FR 11/58598 filed Sep. 27, 2011 and United States Application 61/564,977 filed Nov. 30, 2011, all of which are incorporated herein by reference.

SEQUENCE LISTING

The instant application contains a Sequence Listing which has been submitted in ASCII format via EFS-Web and is hereby incorporated by reference in its entirety. Said ASCII copy, created on Sep. 27, 2012, is named ALB PCT$_{13}$ ST25.txt and is 2.43 kilobytes in size.

TECHNICAL FIELD

The invention relates to a new cosmetic topical use of an extract of *Albizia Julibrissin* and a corresponding topical composition.

The present invention concerns in particular the cosmetics and dermopharmaceutical industries, that produce and/or use products for treating skin, including scalp, mucous membranes and appendages (such as body hair, eyelashes, eyebrows, nails or hairs) of mammals, animals or humans, for increasing the appearance and/or general state.

These industries are in increased demand for new products, particularly in demand for new active ingredients that are derived from plants because they allow combining efficiency, limitation of the risk of irritation and allergies, decrease of side effects, biodegradability, with opportunities of labelling/certifications and suitability with a sustainable development and/or fair trade approach.

The present invention aims to meet this demand.

*Albizia Julibrissin*, also known as Silk Tree or Mimosa of Constantinople, is a deciduous tree of the Mimosaceae family. It is native to East Asia and South America, but it was spread by the man on almost every continent.

*Albizia Julibrissin* extracts have already been proposed in cosmetics.

JP2009242296 discloses an extract of *Albizia Julibrissin* capable of inhibiting action on melanin production and stimulating the production of collagen.

KR20100090530 discloses the inhibitory activity of metallo-proteinases of an extract of *Albizia Julibrissin* cortex.

KR20020080657 discloses an anti-radical activity of an extract of barks of *Albizia Julibrissin*.

JP4342519 discloses the use of an extract of *Albizia Julibrissin* to inhibit the activity of tyrosinase.

JP2000143488 discloses the humectant properties for the skin and hair of an extract of *Albizia Julibrissin*.

JP2048515 discloses the use of an extract of *Albizia Julibrissin* in a hair product to prevent hair loss and promote growth.

JP2010235548 discloses an agent used in cosmetic and food/beverages for whitening skin, restoring hair, providing antioxidant effects and treating diseases e.g. aging, obesity and inflammation, the agent comprising an extract of *Albizia Julibrissin*.

SUMMARY OF THE INVENTION

Figure 1:
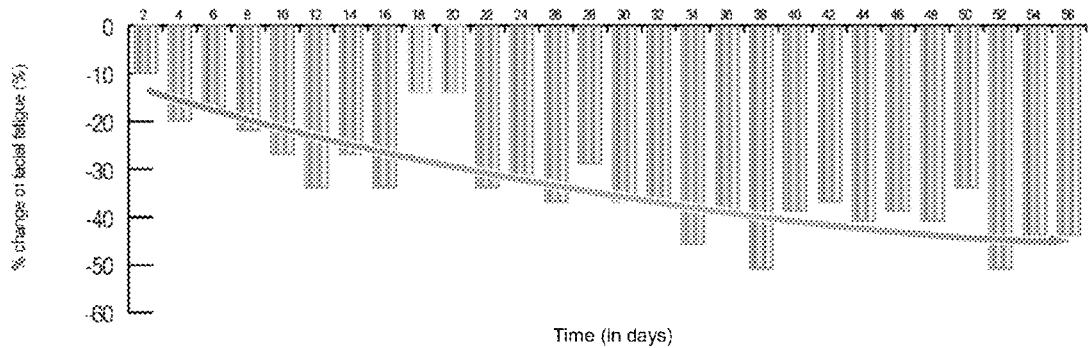
FIG. 1 is a bar graph that represents an aspect of the present invention.

The subject matter of the present invention is the use of an extract of *Albizia Julibrissin* for the topical cosmetic treatment of glycation.

Human body needs sugar, glucose, to produce its energy. Glucose, however, is never entirely used by the body for this beneficial purpose. A residual part of this absorbed sugar will react in a non-enzymatic way with the amine groups of proteins, nucleic acids or lipids to create advanced glycosylated end-products (or AGE products).

AGE formation involves several successive stages. In the early stages, the aldehyde group of a reducing sugar such as glucose forms an unstable bond with the protein amine, known as a Schiff's base, which rapidly rearranges to produce an Amadori compound which is not a final state. This Amadori product undergoes many subsequent reactions, of oxidation, condensation, dehydration, forming intermediate reagents (e.g. aldehydes) to lead to the accumulation of complex end products of advanced glycation (AGEs) that accumulate over time in the tissues.

At the Amadori product stage, the sugar can also deprotonate and create several highly reactive molecules: glyoxal (GO) or its methylglyoxal derivative (MGO), 3-deoxyglucosone (3-DG) or fructosamines. Glyoxals and 3-DG can in turn bind to free protein amines and produce different AGEs such as carboxymethyl-lysine (CML), carboxymethyl-arginine (CMA), carboxymethyl-cysteine (CMC) and their ethyl equivalent or pyrraline, the methyglyoxal-lysine dimer, etc.

The formation of these same reactive chemical forms can also be performed as a result of self-oxidation of glucose, leading to dicarbonylated glycotoxines highly reactive of the glyoxal, methylglyoxal and 3 deoxyglucosone type, these molecules as mentioned above leading to the synthesis of AGEs.

In addition, other sugars such as ribose or xylose although present in smaller amounts are far more reactive than glucose and fructose and also produce AGEs whose in vitro toxicity has been demonstrated.

These different side reactions lead to the formation of many altered proteins (glycated) whose functional, enzymatic and structural properties are impaired with serious consequences on the good functioning of the cell or the organism. Moreover, the binding of nucleic acids to glycotoxins leads to mutations that may be harmful to the cell.

Concerning skin, AGEs are found not only in the dermis but also in the epidermis, as far as the stratum corneum. Organs are even more affected if their proteins have a long life. Thus, collagen of the dermis with a half-life of 15 years is 3 times richer in carboxymethyl-lysine (CML), N-carboxyethyl-lysine (CEL) and pentosidine at the age of 20 years than 80 years. The properties of collagen, along with those of elastin, fibronectin and the laminins, are altered, leading to changes in the mechanical and elastic properties of the extra-cellular matrix of the dermis, which becomes less flexible, more rigid, but also more flaccid and less reactive.

Glycation does not only affect proteins with a long life. Vimentin is an intracellular protein with a far shorter life than collagen. It is an essential component of the intermediate filaments of the cytoskeleton. Vimentin is involved in many functions in cutaneous fibroblasts as healing, mobility and contraction. The AGEs formed from MGO which accumulate in vimentin cause it to aggregate and reduce the contractile ability of the cell and disorganising collagen fibre.

Within the cell, mitochondrial proteins are attacked both directly and indirectly by the glucose which is not used for energy production. These proteins are glycated, causing a fall in the ATP synthesis yield and defective energy production. This process takes place in all of the body compartments, including skin.

The cell also has metabolic sensors or probes which allow regulating its energy production. AMPK (AMP-Activated Protein Kinase) is one of these. This responds to reduced ATP by boosting ATP neosynthesis. The active site for the enzyme is known to be very sensitive to glycation; it may thus lose its regulatory function.

In addition, the AGEs alter vessel permeability by glycation/alteration of their matrix proteins. The micro-inflammatory reactions which occur then lead to reduced flow and leakage of blood components outside of the vessels, causing an accumulation of fluids and waste around them. This leads to the formation of dark circles and some forms of under eye bags.

The AGEs are thus a major source of cellular dysfunction and their progressive accumulation tends to reduce tissue and cell properties and performances: less flexibility, less mobility, less responsive, less energy production. All functions are impaired.

Furthermore, the cell has an active defence mechanism against glycation based on an enzyme system called Glyoxalase-1 and -2 which detoxifies the methylglyoxal and other species of reactive aldehydes via the intervention of GSH. Glycation products tend to reduce glyoxalase activity.

As mentioned above, glycation is a rapid effect and its implications can be quantified in various organs after only a few days of hyperglycaemia. The glycotoxins cause reductions in the cell capacity to produce energy and alterations of macromolecules. The effects of glycotoxins are also cumulative over time. They lead to reduced cell responsiveness to additional stress and lead to a kind of "cellular fatigue" that can be understood by analogy with body fatigue. When the cell (or body) is young, its capacity for recovery is maximal and it therefore recovers quickly. Accumulation of daily fatigue reduces this capacity and amplifies the harmful effects of the glycotoxins.

The transient fatigue becomes usual, then chronic. These signs can be seen on the face: dark circles and under eye bags, dull complexion and drawn facial features, less reactive skin, tired skin. In the cells and tissues, the metabolism is impaired.

Combating cellular fatigue by reducing the daily effects of glycotoxins is therefore an aim to achieve, particularly by protecting melatonin, which is a molecule produced in different parts of the body, particularly in the skin. It has effects on the reparatory regulation of sleep and protective effects, particularly by preserving the cell's energy production capacity. Melatonin levels can be reduced by glycotoxins and maintaining these levels is of direct benefit in preserving the cell's recovery capacity.

The impact on the skin of these biochemical processes, which we have seen the effects at the cellular level, is thus important. Glycation results in dull skin, flaccid skin, without radiance, with a tired appearance, e.g. presenting dark circles and under eye bags, lacking tone and suppleness.

The applicant has shown that an extract of *Albizia Julibrissin* according to the invention presents two decisive and complementary effects to fight glycation:
  Firstly a preventive effect against glycation, to prevent its implementation;
  Secondly a reparative effect, called according to the invention a "deglycating" effect or of "de-glycation" or a detoxifying effect allowing, in a situation where the glycation has begun, to limit the negative consequences, the glycation products being neutralized or detoxified by the extract of *Albizia Julisbrissin*, leading to a reparative effect on tired skin with in particular a loss of radiance and suppleness.

Therefore, according to the invention, the *Albizia Julisbrissin* extract can be used in particular:
  To treat cutaneous fatigue (tired skin); and/or
  To detoxify the skin (including the scalp) and its appendages; and/or
  To improve the brightness or radiance of complexion of the skin and its appendages and treat loss of skin suppleness; and/or
  For the treatment of eye contour, in particular dark circles and under eye bags.

In vivo and in vitro tests are detailed below demonstrating the activity of an *Albizia Julibrissin* extract on the glycation of skin molecules, especially proteins.

In particular, the AGE-Reader™ (DiagnOptics Technologies) is used as a medical device for a non-invasive measurement of the accumulation of AGEs.

"Extract" means according to the invention an extract that can be obtained either by the usual techniques of extraction or by in vitro plant cell culture.

By way of examples, the usual techniques that can be used comprise steeping, simple decoction, lixiviation, extraction under reflux, supercritical fluid extraction, extraction by means of ultrasound or microwaves, or using countercurrent technology. Extraction solvents can be chosen among water, propylene glycol, butylene glycol, glycerin, PEG-6 Caprylic/capric glycerides, polyethylene glycol, methylic and/or ethylic diglycol ethers, cyclic polyols, ethoxylated or propoxylated diglycols, alcohols (methanol, ethanol, propanol, butanol), or any mixture of those solvents.

The invention also covers an extract obtained by in vitro plant culture. Various techniques exist including the culture of undifferentiated or de-differenciated cells, tissue or organ culture or in vitro micropropagation via somatic embryogenesis or by vegetative propagation.

The obtaining of an extract by in vitro plant culture presents advantages over the agro-industrial path (plant culture in open fields and subsequent extraction in factories): the obtained materials are free of toxic substances (herbicides, etc.), reproducibility is improved, biodiversity is preserved, etc.

All parts of the plant, including aerial, such as leaves, flowers or seeds or the roots can be used according to the invention.

Preferably according to the invention, an *Albizia Julibrissin* extract obtained from flowers and/or seeds of the plant, as described below.

According to the invention the *Albizia Julibrissin* extract can be used pure or diluted in a physiologically acceptable excipient or matrix.

The extract is preferably used diluted in a physiologically acceptable excipient or matrix, in particular a hydroglycolic matrix.

The present invention also encompasses a topical composition comprising as an active ingredient which acts on the glycation, an effective amount of an *Albizia Julibrissin* extract in a physiologically acceptable medium. As explained above, the extract of *Albizia Julibrissin* has a remarkable de-glycation effect on proteins or de-toxification of skin.

The topical application may be cosmetic and/or dermopharmaceutical.

According to other advantageous features, the *Albizia Julibrissin* extract can be used in combination with one or more additional active ingredients, preferably to provide a range of wider cosmetic properties. The additional active ingredients can be chosen, for example among the actives for lightening, anti-redness, anti-spot, calming actives, actives for the treatment of sensitive, reactive skin, UV sunscreens, moisturizing, humectant, exfoliating, smoothing, toning, anti-aging, anti-wrinkles and fine lines, actives improving the mechanical and elastic properties, the radiance of complexion, the detoxifying, anti-hair regrowth actives, actives acting on the skin barrier, anti-acne actives, actives acting on the secretion of sebum, matting, unifying, anti-inflammatory, anti-oxidant, anti-radical, anti-glycation actives, actives for the eye contour (dark circles and under eye bags), for a reinforcement of activity, actives promoting blood circulation, peptides, vitamins, etc. These active ingredients can be obtained from plant materials, such as plant extracts or product obtained by plant culture or fermentation.

Surprisingly the present inventors have found that an extract of *Albizia Julibrissin* according to the invention combined with Darutoside was particularly appropriate for treating face, and more particularly the eye contour. Darutoside reinforce and complement the anti-glycation activity of the *Albizia Julibrissin* according the invention for a total eye contour treatment (preventive and curative). Darutoside is a sugar form of Darutigenol and has the following formula:

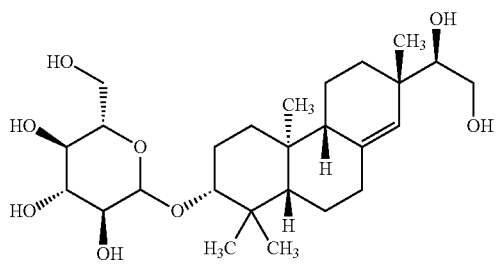

Darutoside can be obtained from any supply source, especially by means of hemi chemical synthesis, chemical synthesis, enzymatic, by one of the many methodologies of biotechnology, by plant extraction or by any other means used to obtain it at reasonable cost in the end-product to be used industrially.

According to an embodiment, the extraction is vegetal, Darutoside being extracted from *Siegesbeckia Orientalis* a plant also known as "holy herb" or "St. Paul's wort". Native to India, *Siegesbeckia Orientalis* has spread to various tropical countries, in particular to Madagascar. It is known as a medicinal plant with soothing and cicatrizing effects. A method of obtaining Darutoside from *Siegesbeckia Orientalis* is disclosed in FR2285142.

Darutoside can also be present in the form of a *Siegesbeckia Orientalis* extract comprising a titrated amount of Darutoside.

Darutoside is formulated in different known marketed cosmetic ingredients. For examples:

Darutoside™ marketed by Sederma: an association of the molecule Darutoside, extracted from *Siegesbeckia orientalis* and an extract from *Centella Asiatica* rich in asiaticoside, which has anti-inflammatory and restructurating properties on dermal extracellular matrix, this ingredient being preconized for the treatment of stretch marks.

Chromocare™ marketed by Sederma: an association of a *Siegesbeckia orientalis* extract rich in Darutoside and an extract of *Rabdosia rubescens* rich in Oridonin, which combats the oxidative stress, and exerts beneficial effect on chromophore ageing (collagen degradation, inflammation and melanin stimulation).

According to present invention a composition comprising an extract of *Albizia Julibrissin* and Darutoside in a physiologically acceptable medium is proposed.

The extract of *Albizia Julibrissin* is an extract as recited above according to the invention.

In vitro tests, detailed after in the specification, show the activity and synergy obtained with the combination according to the invention of the extract of *Albizia Julibrissin* and Darutoside. In particular has been shown:

An increase of gerontogenic genes;
A synergetic action on non-enzymatic glycation of elastin;
An inhibitory activity of metallo-proteinases MMP1 post stress;
An increase of collagen I and elastin.

In vivo tests, also detailed hereafter, show the cosmetic benefit of the combination of the extract of *Albizia Julibrissin* and Darutoside on visible global fatigue of the eye contour: fine lines and wrinkles, eyelids, dark circles and under eye bags.

Other additional active ingredients can be preferably selected from the vitamin B3 compounds, compounds like niacinamide or tocopherol, retinoid compounds such as retinol, hexamidine, α-lipoic acid, resveratrol or DHEA, peptides, in particular N-acetyl-Tyr-Arg-O-hexadecyl ester, Pal-VGVAPG (SEQ ID NO:1), Pal-KTTKS (SEQ ID NO:2), Pal-GHK, Pal-KMO2K and Pal-GQPR (SEQ ID NO:3), which are conventional active ingredients used in topical cosmetic or dermo-pharmaceutical compositions.

The present invention will be better understood in the light of the following description.

DETAILED DESCRIPTION

Composition Preparation

The expression "physiologically acceptable medium" means according to the present invention, without limitation, an aqueous or hydroalcoholic solution, a water-in-oil emulsion, an oil-in-water emulsion, a micro-emulsion, an aqueous gel, an anhydrous gel, a serum, a dispersion of vesicles or a powder.

"Physiologically acceptable" means that the compositions are suitable for topical or transdermal use, in contact with mucous membranes, appendages (nails, hair, body hair), scalp and skin of mammals, particularly human, without risk of toxicity, incompatibility, instability, allergic response, and others.

This "physiologically acceptable medium" forms what is commonly called the excipient of the composition.

For the use according to the invention, the effective amount of *Albizia Julibrissin* extract or of Darutoside if present, that is to say its dosage, depends on various factors such as the age, the state of the skin of the patient, the severity of the disorder or condition and the mode of administration, etc. An effective amount means a not toxic amount enough to achieve the desired effect.

For the anti-glycation and eye contour use according to the invention, the *Albizia Julibrissin* extract or Darutoside if present, to be present in an effective amount, is generally present in an amount ranging from 0.00001% to 90%, more particularly from 0.0001% to 25%, and furthermore particularly from 0.001% to 10% based on the total weight of the composition. The person skilled in the art is able to adjust the amount of extract depending on the desired effect.

All percentages and ratios used herein are by weight of the total composition and all measurements are made at 25° C. unless it is otherwise specified.

The choice of the excipient of the composition is made according to the constraints of the material of *Albizia Julibrissin* and Darutoside if present (stability, solubility, etc.), and if necessary according to the dosage form intended further for the composition.

The *Albizia Julibrissin* extract and Darutoside if present may be incorporated into a composition by means of an aqueous solution, or be dissolved by the usual physiologically acceptable solubilizers, for example and without limiting to this list: ethanol, propanol, isopropanol, propylene glycol, glycerin, butylene glycol, or polyethylene glycol or any combination thereof. It may also be interesting to solubilize the extract with emulsifiers. A powder medium can also be used.

The compositions adapted for the present invention are generally prepared by conventional methods well known to one skilled in the art for making topical and oral compositions and injection compositions. Such methods may involve a mixture of ingredients in one or more steps to obtain a uniform state, with or without heating, cooling, etc.

The different galenic forms that may contain the *Albizia Julibrissin* extract and Darutoside if present of the invention can be all forms i.e. creams, lotions, milks or creams ointments, gels, emulsions, dispersions, solutions, suspensions, cleansers, foundations, anhydrous preparations (sticks in particular lip balm, body and bath oils), shower and bath gels, shampoo and hair care lotions, milks or creams for skin care or hair, cleansing lotions or milks, sunscreen lotions, milks or creams, artificial tanning lotions, milks or creams, pre shave, shaving or aftershave creams, foams, gels or lotions, makeup, lipstick, mascara or nail polish, skin essences, serums, adhesive or absorbent materials, transdermal patches, or emollient powders, lotions, milks or creams, sprays, body and bath oils, foundation basis, ointment, emulsion, colloid, compact suspension or solid, pencil, sprayable formulation, brushable, blush, red, eyeliner, lipliner, lip gloss, face or body powder, styling gels or mousses, nail conditioning, lip balms, skin conditioners, moisturizers, lacquers, soaps, exfoliants, astringents, depilatories agents, permanent waving solutions, antidandruff formulations, antiperspirant or antiperspirant compositions, including sticks, "roll-on" deodorants, air fresheners, sprays for the nose and etc. These compositions may also be in the form of lipsticks intended either to color the lips or to prevent them from chapping, or makeup for eyes, eyeshadows and foundations for the face. The compositions for the invention can include cosmetics, personal care products and pharmaceutical preparations. A composition in the form of foam or in the form of aerosol compositions also comprising a pressurized propellant can be considered. The compositions according to the invention can also be for oral use, for example a toothpaste. In this case, the compositions may contain adjuvants and additives conventional for compositions for oral use, including surfactants, thickening agents, humectants, polishing agents such as silica, various active ingredients such as fluorides, in particular sodium fluoride, and optionally sweeteners such as saccharin sodium.

The *Albizia Julibrissin* extract and Darutoside if present according to the present invention may be in the form of solution, dispersion, emulsion, paste, or powder, individually or as a premix or vehicled individually or as a premix in vectors such as macro-, micro-, or nanocapsules, macro-, micro- or, nanospheres, liposomes, oleosomes or chylomicrons, macro-, micro-, or nanoparticles or macro-, micro or nanosponges, micro- or nanoemulsions, or adsorbed on organic polymer powders, talcs, bentonites, spores or exines, and other inorganic or organic supports.

The *Albizia Julibrissin* extract and Darutoside if present according to the present invention may be used in any form whatsoever, in a form bound to or incorporated in or absorbed in or adsorbed on macro-, micro-, and nanoparticles, or macro-, micro-, and nano-capsules, for the treatment of textiles, natural or synthetic fibers, wools, and any materials that may be used for clothing or underwear for day or night, handkerchiefs or cloths, intended to come into contact with the skin, to exert their cosmetic effect via this skin/textile contact and to permit continuous topical delivery.

Cosmetic Treatment Method

The present invention also proposes a method of cosmetic topical treatment for treating glycation of skin proteins comprising topically applying an effective amount of a composition comprising an *Albizia Julibrissin* extract, as recited above, to the skin of a subject in need thereof.

"Topical treatment" means an application that is intended to act where it is applied: skin, mucosa, skin appendages.

The method according to the invention is specially adapted to:
  To treat tired skin (cutaneous fatigue) that have lost their radiance and suppleness; and/or
  To detoxify the skin (including the scalp) and its appendages; and/or
  To improve the brightness of complexion of the skin and its appendages and treat loss of skin suppleness; and/or
  For the treatment of eye contour, in particular dark circles and under eye bags.

According to other feature of the method the *Albizia Julibrissin* extract is advantageously combined with Darutoside, as recited above, the method being therefore especially adapted to the treatment of tired skin, especially for the eye contour, thanks to a synergetic action on dark circles and under eye bags, wrinkles and fine lines and action on eyelids.

Improvements in the appearance and general condition of the skin, of mucous membranes, and of appendages can be obtained by topical application on a regular basis such as daily.

The practitioner will appreciate the topical cosmetic treatment that will comprise a composition containing the *Albizia Julibrissin* extract, this treatment being achieved for example by applying topically the composition described in the present invention, according to a method usually used to apply such a composition. The topical composition is preferably applied once daily for a period of at least a week, but it can be applied during periods of 2, 4, 8 or 12 weeks. The topical composition is preferably applied to the face and neck, but can be applied to any part of skin requiring an aesthetic improvement, where the composition remains on the skin area to be treated, and preferably is not removed or flushed from the skin. For indication, for a cosmetic face treatment, the European standard dosage of the cream is 2.72 mg/cm$^2$/day/person.

It is also to be understood that, as used herein, the terms treating and treatment include and encompass the reduction, improvement, progress, relief, and/or elimination of dermatological effects, including aging. The compositions of the present invention and the methods are suitable for use to treat skin conditions of the skin in many areas of the skin, including without limitation, the face, forehead, lips, neck, neckline, arms, hands, body, legs, knees, feet, chest, back, buttocks, and others.

One of the major advantages of the present invention resides in the ability whenever necessary or desirable to be able to apply local selective "gentle" treatments through this topical, non-invasive method of application. In the case of anti-wrinkle use for example it may be applied very locally using a syringe or micro-canula.

It is also possible, however, to consider a composition according to the invention intended to be injected subcutaneously.

According to other specific features, the cosmetic treatment method according to the invention can be combined with one or more other treatment methods targeting the skin such as lumino-therapy, heat or aromatherapy treatments.

According to the invention, devices with several compartments or kits may be proposed to apply the method described above which may include for example and non-restrictively, a first compartment containing a composition comprising the *Albizia Julibrissin* extract of the invention, and in a second compartment a composition containing another active ingredient, like the Darutoside, and/or excipient, the compositions contained in the said first and second compartments in this case being considered to be a combination composition for simultaneous, separate or stepwise use in time, particularly in one of the treatment methods recited above.

Additional Ingredients

The CTFA International cosmetic ingredient dictionary & handbook (13th Ed. 2010) (published by the Cosmetic, Toiletry, and Fragrance Association, Inc., Washington, D.C.) describes a non-limited wide variety of cosmetic and pharmaceutical ingredients conventionally used in the skin care industry that can be used as additional ingredients/compounds in the compositions for the present invention. Examples of these ingredient classes include, but are not limited to: healing agents, skin anti-aging agents, anti-wrinkle agents, anti-atrophy agents, skin moisturizing agents, skin smoothing agents, antibacterial agents, antiparasitic agents, antifungal agents, fungicidal agents, fungistatic agents, bactericidal agents, bacteriostatic agents, antimicrobial agents, anti-inflammatory agents, anti-pruriginous agents, anesthetic agents, antiviral agents, keratolytic agents, free radicals scavengers, anti-seborrhea agents, anti-dandruff agents, the agents modulating differentiation, proliferation or pigmentation of the skin and agents accelerating penetration, desquamating agents, melanin synthesis stimulating or inhibiting agents, whitening, depigmenting or lightening agents, pro-pigmenting agents, self-tanning agents, NO-synthase inhibiting agents, antioxidants, free radical scavengers and/or agents against atmospheric pollution, reactive carbonyl species scavengers, anti-glycation agents, tightening agents, agents stimulating the synthesis of dermal or epidermal macromolecules and/or capable of inhibiting or preventing their degradation, such as for example collagen synthesis stimulating agents, elastin synthesis stimulating agents, decorin synthesis stimulating agents, laminin synthesis stimulating agents, defensin synthesis stimulating agents, chaperone synthesis stimulating agents, aquaporin synthesis stimulation agents, hyaluronic acid synthesis stimulating agents, fibronectin synthesis stimulating agents, sirtuin synthesis-stimulating agents, agents stimulating the synthesis of lipids and components of the stratum corneum (ceramides, fatty acids, etc.), collagen degradation inhibiting agents elastin degradation inhibiting agents, agents stimulating fibroblast proliferation, agents stimulating keratinocyte proliferation, adipocyte proliferation stimulating agents, melanocyte proliferation stimulating agents, keratinocyte differentiation stimulating agents, adipocyte differentiation stimulating agents, acetylcholinesterase inhibiting agents, glycosaminoglycan synthesis stimulating agents, DNA repair agents, DNA protecting agents, anti-itching agents, agents for the treatment and/or care of sensitive skin, firming agents, anti-stretch mark agents, astringent agents, sebum production regulating agents, dermo-relaxing agents, healing adjuvant agents, re-epithelialization stimulating agents, re-epithelialization co-adjuvant agents, cytokine growth factors, calming agents, anti-inflammatory agents, agents acting on capillary circulation and/or microcirculation, angiogenesis stimulating agents, vascular permeability inhibiting agents, agents acting on cell metabolism, agents able to improve dermal-epidermal junction, agents inducing hair growth, hair growth inhibiting or retardant agents, muscle relaxants agents, antipollution and/or anti-free radical agents, lipolysis stimulating agents, slimming agents, anti-cellulite agents, agents acting on the microcirculation, agents acting on the energy metabolism of the cells, cleaning agents, hair conditioning agents, hair styling agents, hair growth promoters, sunscreen agents, total sunscreen agents, make-up agents, detergents, pharmaceutical products, emulsifiers, emollients, organic solvents, antiseptic agents, deodorant actives, physiologically acceptable carriers, surfactants, abrasives, absorbents, aesthetic components such as fragrances, pigments, dyes, colorants, natural colorants, essential oils, touch agents, cosmetic astringents, anti-acne agents, anti-coagulation agents, anti-foaming agents, antioxidants, binders, biological additives, enzymes, enzymatic inhibitors, enzyme-inducing agents, coenzymes, chelating agents, plant extracts, plant derivatives, essential oils, marine extracts, agents obtained from a bio-fermentation or a biotechnological process, mineral salts, cell extracts, sunscreens (organic or mineral photoprotective agents active against ultraviolet A and/or B rays), ceramides, peptides, buffers, volumizing agents, chelating agents, chemical additives, colorants, cosmetic biocides, denaturants, medical astringents, external analgesics, film formers, such as polymers, for exacerbing film-forming properties and substantivity of the composition, quaternary derivatives, substantivity increasing agents, opacifying agents, pH adjusters and regulators (e.g. triethanolamine), propellants, reducing agents, sequestrants, decoloring and/or lightening agents, skin-conditioning agents (e.g., humectants, including miscellaneous and occlusive), moisture retaining agents, alpha-hydroxyacids, betahydroxyacids, moisturizers, epidermal hydrolytic enzymes, healing and/or calming agents, skin treating agents, anti-wrinkle agents, agents that reduce or treat bags under the eyes, exfoliating agents, thickeners, softening agents, gelling polymers, vitamins and their derivatives, wetting agents, peeling agents, soothing agents, curative agents of the skin, lignans, preservatives (i.e. phenoxyethanol and parabens), anti UV, cytotoxic agents, antineoplastics, viscosity modifiers, non-volatile solvents, pearling agents, anti-perspirant agents, depilatories, vaccine, perfumed water, skin restructuring agent (i.e. *Siegesbeckia orientalis* extract), excipients, charges, minerals, anti-mycobacterial agents, anti-allergenic agents, H1 or H2 antihistaminics, anti-irritants, agents stimulating the immune system, agents inhibiting the immune system, insect repellents, lubricants, pigments or dyes, hypopigmentation agents, preservatives, light stabilizers, and mixtures thereof, as long as they are physically and chemically compatible with the other ingredients of the composition and especially with the active ingredients of the present invention. Also the nature of these additional ingredients should not unacceptably alter the benefits of the active ingredients of the invention. These additional ingredients can be synthetic or natural such as plants extracts, or come from a bio-fermentation process. Additional examples can be found in the CTFA Cosmetic Ingredient Handbook.

Such additional active ingredient/compound can be selected from the group consisting of: sugar amines, glucosamine, D-glucosamine, N-acetyl glucosamine, N-acetyl-D-glucosamine, mannosamine, N-acetyl mannosamine, galactosamine, N-acetyl galactosamine, B3 vitamin and its derivatives, niacinamide, sodium dehydroacetate, dehydroacetic acid and its salts, phytosterols, salicylic acid compounds, hexamidines, dialkanoyl hydroxyproline compounds, soy extracts and derivatives, equol, isoflavones, flavonoids, phytantriol, farnesol, geraniol, bisabolol, peptides and their derivatives, di-, tri-, tetra-, penta-, and hexa-peptides and their derivatives, KTTKS (SEQ ID NO: 4), Pal-KTTKS (SEQ ID NO: 2), carnosine, N-acyl amino acid compounds, retinoids, retinyl propionate, retinol, retinyl palmitate, retinyl acetate, retinal, retinoic acid, water-soluble vitamins, ascorbates, C vitamin, ascorbyl glucoside, ascorbyl palmitate, magnesium ascorbyl phosphate, sodium ascorbyl phosphate, vitamin B and their salts and derivatives, B1 vitamin, B2 vitamin, B6 vitamin, B12 vitamin, provitamins and their salts and derivatives, K vitamin and derivatives, pantothenic acid and its derivatives, pantothenyl ethyl ether, panthenol and derivatives, dexpanthenol, biotin, amino acids and their salts and derivatives, water soluble amino acids, asparagine, alanine, indole, glutamic acid, water insoluble vitamins, A vitamin, E vitamin, F vitamin, D vitamin and mono-, di-, and tri-terpenoids compounds, beta-ionol, cedrol, and their derivatives, water insoluble amino acids, tyrosine, tryptamine, particulate materials, butylated hydroxytoluene, butylated hydroxyanisole, allantoin, tocopherol nicotinate, tocopherol, tocopherol esters, palmitoyl-Gly-His-Lys (Pal-GHK), phytosterol, hydroxy acids, glycolic acid, lactic acid, lactobionic acid, keto acids, pyruvic acid, phytic acid, lysophosphatidic acid, stilbenes, cinnamates, resveratrol, kinetin, zeatin, dimethylaminoethanol, natural peptides, soy peptides, salts of sugar acids, Mn gluconate, Zn gluconate, piroctone olamine, 3,4,4'-trichlorocarbanilide, triclocarban, Zn pyrithione, hydroquinone, kojic acid, ascorbic acid, magnesium ascorbyl phosphate, ascorbyl glucoside, pyridoxine, aloe vera, terpene alcohols, allantoin, bisabolol, dipotassium glycyrrhizinate, glycerol acid, sorbitol acid, pentaerythritol acid, pyrrolidone acid and salts, dihydroxyacetone, erythrulose, glyceraldehyde, tartaraldehyde, clove oil, menthol, camphor, *eucalyptus* oil, eugenol, menthyl lactate, witch hazel distillate, eicosene and vinyl pyrrolidone copolymer, iodopropyl butylcarbamate, a polysaccharide, an essential fatty acid, a salicylate, glycyrrhetinic acid, carotenoids, ceramides and pseudo-ceramides, a lipid complex, oils in general of natural origin such shea butter, apricot oil, onagre oil, prune oil, palm oil, monoi oil, hydroquinone, HEPES, procysteine, O-octanoyl-6-D-maltose, the disodium salt of methylglycinediacetic acid, steroids such as diosgenin and derivatives of DHEA, DHEA or dehydroepiandrosterone and/or a precursor or chemical or biological derivative thereof, N-ethyloxycarbonyl-4-para-aminophenol, blueberries extracts, phytohormones, extracts of the yeast *Saccharomyces cerevisiae*, extracts of algae, extracts of soyabean, lupin, maize and/or peas, alverine and its salts, in particular alverine citrate, extract of butcher's broom and of horse chestnut, octadecenedioic acid, analogs and derivatives, and mixtures thereof, a metalloproteinase inhibitor.

Further skin care and hair care active ingredients that are particularly useful combined with the composition can be found in SEDERMA commercial literature and on the website www.sederma.fr.

The following commercial actives can also be mentioned, as examples: betain, glycerol, Actimoist Bio 2™ (Active organics), AquaCacteen™ (Mibelle AG Cosmetics), Aquaphyline™ (Silab), AquaregulK™ (Solabia), Carciline™ (Greentech), Codiavelane™ (Biotech Marine), Dermaflux™ (Arch Chemicals, Inc), Hydra'Flow™ (Sochibo), Hydromoist L™ (Symrise), RenovHyal™ (Soliance), Seamoss™ (Biotech Marine), Essenskin™ (Sederma), Moist 24™ (Sederma), Argireline™ (trade name of the acetyl hexapeptide-3 of Lipotec), spilanthol or an extract of *Acmella oleracea* known under the name Gatuline Expression™, an extract of *Boswellia serrata* known under the name Boswellin™, Deepaline PVB™ (Seppic), Syn-AKE™ (Pentapharm), Ameliox™, Bioxilift™ (Silab), Juvinity™ (Sederma), Revidrate™ (Sederma), Chronodyn™ (Sederma), O.D.A. White™ (Sederma), Idealift™ (Sederma), Resistem™ (Sederma), Widelash™ (Sederma) or mixtures thereof.

Among other plant extracts which can be combined with the composition of the invention, there may more particularly be mentioned extracts of Ivy, in particular English Ivy (*Hedera Helix*), of *Bupleurum chinensis*, of *Bupleurum Falcatum*, of *arnica* (*Arnica Montana* L), of rosemary (*Rosmarinus officinalis* A), of marigold (*Calendula officinalis*), of sage (*Salvia officinalis* L), of ginseng (*Panax ginseng*), of ginko biloba, of St.-John's-Wort (*Hyperycum Petforatum*), of butcher's-broom (*Ruscus aculeatus* L), of European meadowsweet (*Filipendula ulmaria* L), of big-flowered Jarva tea (*Orthosiphon Stamincus Benth*), of *algae* (*Fucus Vesiculosus*), of birch (*Betula alba*), of green tea, of cola nuts (*Cola Nipida*), of horse-chestnut, of bamboo, of *Centella asiatica*, of heather, of fucus, of willow, of mouse-ear, of escine, of cangzhu, of *chrysanthellum indicum*, of the plants of the Armeniacea genus, *Atractylodis Platicodon, Sinnomenum, Pharbitidis, Flemingia*, of *Coleus* such as *C. Forskohlii, C. blumei, C. esquirolii, C. scutellaroides, C. xanthantus* and *C. Barbatus*, such as the extract of root of *Coleus barbatus*, extracts of *Ballote*, of *Guioa*, of *Davallia*, of *Terminalia*, of *Barringtonia*, of *Trema*, of *antirobia, cecropia, argania, dioscoreae* such as *Dioscorea opposita* or Mexican, extracts of *Ammi visnaga*, of *Siegesbeckia*, in particular *Siegesbeckia orientalis*, vegetable extracts of the family of Ericaceae, in particular bilberry extracts (*Vaccinium angustifollium*) or *Arctostaphylos uva ursi*, aloe vera, plant containing sterols (e.g., phytosterol), Manjistha (extracted from plants of the genus *Rubia*, particularly *Rubia Cordifolia*), and Guggal (extracted from plants of the genus *Commiphora*, particularly *Commiphora Mukul*), kola extract, chamomile, red clover extract, *Piper methysticum* extract (Kava Kava™ from SEDERMA), Bacopa monieri extract (Bacocalmine™ from SEDERMA) and sea whip extract, extracts of *Glycyrrhiza glabra*, of mulberry, of *melaleuca* (tea tree), of *Larrea divaricata*, of *Rabdosia rubescens*, of *Euglena gracilis*, of *Fibraurea recisa Hirudinea*, of *Chaparral Sorghum*, of sun flower extract, of *Enantia chlorantha*, of Mitracarpe of *Spermacocea* genus, of *Buchu barosma*, of *Lawsonia inermis* L., of *Adiantium Capillus-Veneris* L., of *Chelidonium majus*, of *Luffa cylindrica*, of Japanese Mandarin (*Citrus reticulata Blanco* var. *unshiu*), of *Camelia sinensis*, of *Imperata cylindrica*, of *Glaucium Flavum*, of *Cupressus Sempervirens*, of *Polygonatum multiflorum*, of *loveyly hemsleya*, of *Sambucus Nigra*, of *Phaseolus lunatus*, of *Centaurium*, of *Macrocystis Pyrifera*, of *Turnera Diffusa*, of *Anemarrhena asphodeloides*, of *Portulaca pilosa*, of *Humulus lupulus*, of *Coffea Arabica*, of *Ilex Paraguariensis*, of *Zingimber Zerumbet* Smith, of *Globularia Cordifolia*, or of *Ulva Lactuca*.

The compositions of the present invention may include peptides, including, without limitation, the di-, tri-, tetra-, penta- and hexapeptides and their derivatives. According to a particular embodiment, the concentration of the additional peptide, in the composition, ranges from $1\times10^{-7}\%$ and 20%, preferably from $1\times10^{-6}\%$ and 10%, preferably between $1\times10^{-5}\%$ and 5%, by weight.

According to the present invention, the term "peptide" refers to peptides containing 10 amino acids or less, their derivatives, isomers and complexes with other species such as a metal ion (e.g. copper, zinc, manganese, magnesium, and others). The term "peptides" refers to both natural peptides and synthetic peptides. It also refers to compositions that contain peptides which are found in nature, and/or are commercially available.

Suitable dipeptides for use herein include but are not limited to carnosine (beta-AH), YR, VW, NF, DF, KT, KC, CK, KP, KK or TT. Suitable tripeptides for use herein include, but are not limited to RKR, HGG, GHK, GKH, GGH, GHG, KFK, KPK, KMOK, $KMO_2K$ or KAvaK. Suitable tetrapeptides for use herein include but are not limited to RSRK (SEQ ID NO: 5), GQPR (SEQ ID NO: 6) or KTFK (SEQ ID NO: 7). Suitable pentapeptides include, but are not limited to KTTKS (SEQ ID NO: 4). Suitable hexapeptides include but are not limited to GKTTKS (SEQ ID NO: 8), VGVAPG (SEQ ID NO: 9).

Other suitable peptides for use herein include, but are not limited to lipophilic derivatives of peptides, preferably palmitoyl derivatives, and metal complexes as aforementioned (e.g. copper complex of the tripeptide HGG). Preferred dipeptide derivatives include N-Palmitoyl-beta-Ala-His, N-Acetyl-Tyr-Arg-hexadecylester (Calmosensine™, Idealift™ from Sederma). Preferred tripeptide derivatives include N-Palmitoyl-Gly-Lys-His, and Pal-Gly-His-Ly, (Pal-GKH and Pal-GHK from Sederma), the copper derivative of HGG (Lamin™ from Sigma), Lipospondin (N-Elaidoyl-KFK) and its analogs of conservative substitution, N-Acetyl-RKR-NH2 (Peptide CK+), N-Biot-GHK (from Sederma), Pal-KMO2K (Sederma) and derivatives thereof. Suitable tetrapeptide derivatives for use according to the present invention include, but are not limited to, N-palmitoyl-GQPR (SEQ ID NO: 3) (from Sederma), suitable pentapeptide derivatives for use herein include, but are not limited to, N-Palmitoyl-KTTKS (SEQ ID NO: 2) (available as Matrixyl™ from Sederma), N-Palmitoyl-Tyr-Gly-Gly-Phe-X (SEQ ID NO: 10) with X Met or Leu or mixtures thereof. Suitable hexapeptide derivatives for use herein include, but are not limited to, N-Palmitoyl-VGVAPG (SEQ ID NO: 1) and derivatives thereof. The mixture of Pal-GHK and Pal-GQPR (SEQ ID NO: 3) (Matrixyl™ 3000, Sederma) can also be mentioned.

The preferred compositions commercially available containing a tripeptide or a derivative include Biopeptide-CL™, Maxilip™, Biobustyl™, Procapil™ and MatrixylTmsynthe'6™ of Sederma. The compositions commercially available preferred sources of tetrapeptides include Rigin™, Eyeliss™ Matrixyl™ Reloaded and Matrixyl 3000™ which contain between 50 and 500 ppm of Palmitoyl-GQPR (SEQ ID NO: 3) and carrier, proposed by Sederma.

The following marketed peptides can be mentioned as well as additional active ingredients: Vialox™ Syn-ake™ or Syn-Coll™ (Pentapharm), Hydroxyprolisilane CN™ (Exsymol), Argireline™ Leuphasyl™, Aldenine™, Trylgen™, Eyeseryl™, Serilesine™ or Decorinyl™ (Lipotec), Collaxyl™ or Quintescine™ (Vincience), BONT-L-Peptide™ (Infinitec Activos), CytokinolTMLS (Laboratoires Serobiologiques/Cognis), Kollaren™, IP2000™ or Meliprene™ (Institut Europeen de Biologie Cellulaire), Neutrazen™ (Innovations), ECM-Protect™ (Atrium Innovations), Timp-Peptide™ or ECM Moduline™ (Infinitec Activos).

A) Examples of Obtaining an *Albizia Julibrissin* Extract that can be Used According to the Invention Example 1 of procedure: a hot extraction under reflux of *Albizia Julibrissin* seeds is carried out using an alcohol or mixture of alcohols, preferably ethanol. After removal of the alcohol, the residue is taken up by a glycerin/water mixture.

Alternatively, the extraction can be performed with a mixture of alcohol(s)/water.

Example 2 of procedure: a hot aqueous extraction under reflux of flowers *Albizia Julibrissin* is performed. The extract obtained is mixed with glycerol to form a hydroglycolic mixture.

The hydro-glycolic extract of *Albizia Julibrissin* thus obtained is titrated in albizzine identified by HPLC chromatography. It can be used directly in a galenic formulation or be further diluted in an excipient to form an "active ingredient" for future galenic formulations as explained below.

B) Formulation of an <<Active Ingredient>>

The active ingredient is a composition comprising the hydro-glycolic *Albizia Julibrissin* extract obtained according to A) above dissolved in a matrix forming a physiologically acceptable medium. This active ingredient is particularly intended for the cosmetic industry for preparing cosmetics formulations, like creams, gels, etc. (see the galenic examples given below).

An effective amount, i.e. between 1% and 15%, of an extract of *Albizia Julibrissin* obtained according to A) above titrated at 2% of albizine may be mixed to all hydrophilic matrix such as a gel, an aqueous buffer, glycerin or any other polyol with a short chain physiologically acceptable.

For example, and for the description of the in vivo tests and galenic, it is this 7.5% hydro-glycolic extract in glycerin which was preferably used. This is the active ingredient which will be formulated itself preferably between 1 and 5% in a cosmetic composition applicable to the skin.

According to the invention, the active ingredient can also be a composition comprising the *Albizia Julibrissin* extract combined with Darutoside.

An effective amount, i.e. between 1% and 15%, of an extract of *Albizia Julibrissin* obtained according to A) above titrated at 2% of albizine may be mixed with an effective amount, i.e. between 0.01% and 1% of Darutoside in all hydrophilic matrix such as a gel, an aqueous buffer, glycerin or any other polyol with a short chain physiologically acceptable.

As an example, which was used for the in vivo tests and for examples of galenic formulation given below, an active ingredient was prepared comprising 7.5% of the hydrogycolic extract of *Albizia Julibrissin* titrated at 2%+0.05% of Darutoside (extracted from *Siegesbeckia Orientalis*; powder form) in a butylene glycol matrix. This active ingredient will be formulated itself preferably between 1 and 5% in a cosmetic composition applicable to the skin.

C) In Vitro Tests; Anti-Glycation Activity of the *Albizia Julibrissin* Extract

The anti-glycation activity according to the invention of the *Albizia Julibrissin* extract has been shown in the in vitro tests given below.

For the tests achieved on cell cultures, a hydro-glycolic extract obtained according to Example A) above comprising 2% of albizine was used at 0.006% diluted in aqueous excipients, of the type of cell culture media.

1. Improvement of the Dermal Fiber Quality a. Measurement of Carboxymethyl-Lysine (CML) in Fibroblasts Principle and protocol: CML, a specific type of AGEs, accumulates during time in particular on the dermis proteins synthesized by fibroblasts. In vitro, on fibroblasts in culture, it is possible to accelerate this phenomenon by a glycating stress.

500 µM of methylglyoxal (MGO) were applied to confluent human dermal fibroblasts (HDF) to provoke AGE formation. After this glycating contact at 37° C. during 4 days, the MGO was removed from the cultures by rinsing and the *Albizia Julibrissin* extract was applied for 5 days. The supernatants were then removed for Elisa measurement of CML released by the fibroblasts. Cells were counted in parallel from the cell layers. Two independent tests were performed.

Results: The *Albizia Julibrissin* extract did not produce any change in cell numbers. Treatment with MGO reduced survival by 44% and increased CML by 124% ($p<0.01$ compared to the control).

In parallel, the *Albizia Julibrissin* extract reduced CML by 43% ($p<0.05$; compared to the control with MGO). This test highlights the de-glycating feature of the extract according to the invention, because it reduces CML after the action of the glycating agent.

TABLE 1

Change in CML in cultured fibroblasts

| | Concentration | CML (ng/mL/10$^6$cell.) | % Change; significance | |
|---|---|---|---|---|
| Fibroblasts; n = 5 | Control without MGO | 549 ± 66 | Reference 1 | — |
| | Control with MGO | 1231 ± 117 | +124%; p < 0.01 | Reference 2 |
| | MGO and *Albizia Julibrissin* extract | 705 ± 171 | — | −43%; p < 0.05 |

Positive control aminoguanidine 0.03%; −41% CML; (p < 0.01).

b. Reduction in AGEs in Explants

Principle and protocol: Human abdominal skin explants from a 34-year-old woman were placed in contact with the glycating agent MGO dissolved in the survival medium. After the glycation phase, the skins (n=5/case) received an application of a cream comprising the *Albizia Julibrissin* extract or a placebo cream (cream according to example 1 of the galenic paragraph). Topical applications were administered once per day for 4.5 days. The skin sections were then included and cut with a microtome before being labelled with a fluorescent anti-AGE antibody. 10 photos/case were taken and analyzed on suitable software.

Results: The results show that AGE labelling was located particularly in the dermis, an area which is rich in stable matrix proteins (in particular collagen). Quantifications were therefore carried out in this area.

TABLE 2

Change in AGEs on skin explants

| | Concentration | AGEs (AFU*) | % Change; significance |
|---|---|---|---|
| Explants; n = 5 | MGO then the Placebo cream | 9.56 ± 1.30 | Reference |
| | MGO then the cream comprising the *Albizia Julibrissin* | 7.33 ± 1.40 | −23.4%; p < 0.01 |

*AFU = Arbitrary fluorescence unit

Treatment of the explants with MGO followed by applications of the placebo cream resulted in 23% greater AGE labelling compared to the explants which had received the cream comprising *Albizia Julibrissin* ($p<0.01$). This demonstrates a de-glycation phenomenon; the presence of the extract of *Albizia Julibrissin* who helped rid the explant of a part of AGEs formed (by reference to the control).

c. Reduction in Vimentin Damage

Principle and protocol: Just like the proteins with a long half-life such as collagen, proteins with a shorter half-life can be altered by glycotoxins. Vimentin, whose role in the organisation of cellular contraction and cohesion of the dermis was noted above, was studied in this test. This protein is also known to be sensitive, particularly to MGO which forms CML. It is therefore important to protect it. The same explants as above (point 1b) were used to perform a labelling of vimentin using a fluorescent anti-vimentin antibody and the same methods were used for quantification Results: The photographs show vimentin labelling in the upper part of the dermis. Quantifications were therefore performed on this area.

TABLE 3

Change in vimentin labelling on skin explants

| | Concentration | Vimentin (AFU*) | % change; significance |
|---|---|---|---|
| Explants; n = 5 | MGO then the Placebo cream | 3.53 ± 0.90 | Reference |
| | MGO then the cream comprising the *Albizia Julibrissin* | 6.17 ± 2.10 | 75%; p < 0.01 |

*UFA = Arbitrary fluorescence unit

The beneficial effect of the *Albizia Julibrissin* extract against glycating stress clearly appears as the extract seems to have "de-glycated" an important part of vimentin that had been glycated in the initial phase (by reference to the control).

a. Improvement in Contractile Capacity

Principle and protocol: Glycotoxins change the mechanical properties of dermal collagen and elastin proteins, this leading to disorganisation and rigidifying of dermis.

Gels comprising collagen I and III and dermal human fibroblasts were manufactured were prepared (n=4/case). After polymerisation, the gels were treated with MGO ±*Albizia Julibrissin* extract for 5 days. Contraction was monitored with a CCD camera. The difference between the gel surface at T0 and T5 days is a good indicator of gel contraction.

Results: The MGO treatment of the placebo gel reduces its contraction by 78%, which can be attributed to reduced survival of fibroblasts and disruption of the gel by the formed AGEs. If stress cases are compared, the extract of *Albizia Julibrissin* improves contraction of 68% compared to control.

TABLE 4

Change in dermal lattice contraction

| | Concentration | Difference in contraction (mm²) | % Change; significance | |
|---|---|---|---|---|
| Lattices; n = 4 | Control without MGO | 38.9 ± 7.5 | Reference 1 | — |
| | Control with MGO | 8.7 ± 1.9 | −78%; p < 0.01 | Reference 2 |
| | MGO and *Albizia Julibrissin* extract | 14.5 ± 3.2 | — | +68%; p < 0.01 |

2. Improvement of the Respiratory Capacity a. Improvement of the Contractile Capacities in an ATP Shortage Situation Principle and protocol: Gels comprising collagen I and III and dermal human fibroblasts were prepared (n=4/case). After polymerization, the gels received 2DG (2-deoxyglucose), a non-energetic analogue of glucose (non glycating), reversible inhibitor of the formation of ATP. These cultures have also received or not the *Albizia Julibrissin* extract for 5 days. Contraction was monitored with a CCD camera. The difference between the gel surface at T0 and this same surface at T5 days is a good indicator of gel contraction.

Results: The control gels contracted as expected. With the control case, the 2DG treatment, by reducing ATP supply, reduces contraction by 75% without altering survival. Despite ATP deficiency (with 2DG), the *Albizia Julibrissin* extract improves contraction by 98% ($p<0.05$; compared to the control case). The extract therefore allows the cells to better maintain their contractile properties despite ATP deficiency.

TABLE 5

Change in contraction of dermal lattices after contact with 2DG

| | Concentration | Difference in contraction (mm²) | % Change; significance | |
|---|---|---|---|---|
| Lattices; n = 3 | Control without 2DG | 78.3 ± 6.2 | Reference 1 | — |
| | Control with 2DG | 19.5 ± 7.3 | −75%; p < 0.01 | Reference 2 |
| | 2DG and *Albizia Julibrissin* extract | 38.6 ± 11.7 | — | +98%; p < 0.05 | b. Improvement of the Respiratory Capacity Under "fatiguing" Stress

Principle and Protocol: The culture protocol below is intended to simulate the phases of fatigue and rest of the cell. HDF were cultured continuously for 16 days with or without the *Albizia Julibrissin* extract. On day 4 and day 13, the cells were fatigue-stressed with $500_,1$ M of MGO for 3 days. ATP was measured at the end point in all cases (n=5/cases; 2 independent tests).

Results: In the absence of glycating treatment, there is no significant difference between the control case and the case with the *Albizia Julibrissin* extract.

In the control case, treatment with MGO (glycating stress) greatly reduces the ATP amount compared to the non-glycated case (−74%). In the case of glycating treatment in the presence of the *Albizia Julibrissin* extract, ATP synthesis is 182% compared to the glycated control case. The *Albizia Julibrissin* extract therefore enables the cells to maintain a good level of ATP synthesis compared to control, despite the glycating stress.

TABLE 6

| | | ATP (nM/10$^6$ cell.) | % Change; significance | |
|---|---|---|---|---|
| Fibroblasts; n = 5 | Control without MGO | 19.0 ± 5.0 | Reference 1 | — |
| | Control with MGO | 4.9 ± 1.8 | −74%; p < 0.01 | Reference 2 |
| | MGO and *Albizia Julibrissin* extract | 13.9 ± 1.9 | — | +182%; p < 0.01 | c. Preservation of the AMPK Energy Sensor

Glycotoxins reduce the functional capacity of mitochondria, particularly by changing their respiration enzymes. Glycotoxins also attack some intracellular sensors responsible for detecting fluctuations in AMP and ATP levels, such as the AMP-dependent kinase (pAMPK) and thereby regulates the intensity of the cell breathing as needed. A fast and responsive energy production requires that this enzyme be not glycated and retains its properties intact.

Principle and protocol: Human abdominal skin explants from a 34-year-old woman were placed in contact with MGO dissolved in the survival medium. After the glycation phase, the skin (n=5/case) received an application of the *Albizia Julibrissin* extract or the placebo cream. Topical applications were administered once per day for 4.5 days. The skin sections were cut with a microtome before being labelled with a fluorescent anti-pAMPK antibody. 10 photos/case were taken and analysed on suitable software.

Results: Results show that pAMPK labelling was located particularly in the epidermis where the quantifications were performed. Topical application of the cream containing the *Albizia Julibrissin* extract allowed the cell to better preserve the energy sensor AMPK, compared to control cases. Therefore the extract seems to have "deglycated" a part of the enzyme that had been glycated in the initial phase.

TABLE 7

| Concentration | pAMPK (AFU*) | % Change; significance |
|---|---|---|
| Control with MGO | 0.87 ± 0.30 | Reference |
| MGO and *Albizia Julibrissin* extract | 1.09 ± 0.40 | +25%; p < 0.01 |

*AFU = Arbitrary fluorescence unit

3. Glycotoxin Detoxification Systems a. Maintenance of Glyoxalase-1

Principle and protocol: As seen before, MGO and GO can be neutralised as soon as they are formed by glyoxalase-1 which prevents the formation of the resultant glycotoxins and amplification of the synthesis of these pro-glycating agents.

500 µM of Methylglyoxal (MGO) was applied to confluent human dermal fibroblasts in order to provoke glycotoxin formation in their extracellular matrix. After the glycating contact period at 37° C., the MGO was removed from the cultures by rinsing and the *Albizia Julibrissin* extract was applied for 5 days. The cell layers were then extracted and residual glyoxalase-1 was quantified by Western Blot. The comparison was made with an equivalent amount of proteins (protein assay by BCA).

Results: In the absence of glycating treatment, there is no significant difference between the control case and the case with the *Albizia Julibrissin* extract. In the control case, the glycating treatment causes a fall in glyoxalase-1 synthesis of 56% (p<0.01 compared to the non-glycated control). Further to the glycating treatment in the presence of the *Albizia Julibrissin* extract, there are 41% more glyoxalase compared to the glycated case control. The extract according to the invention seems to have deglycated an important part of the enzyme that had been glycated in the initial phase of the culture.

B. Maintaining the Activity of Proteasome

Principle and protocol: The proteasome is an intracellular protein structure dedicated to the regular cellular content purification of damaged proteins, in particular damaged by glycating stresses, and thus can become toxic. The proteasome is sensitive to glycotoxins either directly by a glycating or indirectly if ATP synthesis lower, because it is ATP dependent.

Serum albumin (BSA) was used as a protein model. BSA was glycated in contact with MGO for a week. Subsequently, this glycotoxin (glycated BSA) was incubated for 6 days with or without the *Albizia Julibrissin* extract.

Each of the two solutions was brought into contact with human dermal fibroblasts at confluence for 3 days, in order to induce an alteration of the proteasome by the glycated protein. Following this contact, and after rinsing, the cells were crushed and a determination of proteasome activity was performed.

Results: In the absence of glycating treatment, the *Albizia Julibrissin* extract has no effect on the activity of the proteasome. These results show that model glycotoxin (BSA-AGE) significantly reduces by its contact with the cells, the activity of the purification system of the cell, the proteasome, by 16% (two independent experiments). This test shows that can extracellular glycotoxins can modulate actions in the cell via different metabolic pathways. The same BSA-AGE complex in contact for 6 days with the *Albizia Julibrissin* extract lost its toxicity and became unable to reduce the proteasome activity in human dermal fibroblasts. It can be assumed that the glycotoxin model (BSA-AGE) was detoxified (deglycated) by 6 days contact with the extract of *Albizia Julibrissin*.

TABLE 8

Change in the proteasome activity after contacting with BSA-AGE.

| | | Proteasome activity* | % Change; significance | |
|---|---|---|---|---|
| Fibroblasts; n = 5 | Control without BSA | 971 ± 64 | Reference 1 | — |
| | Control with BSA-AGE | 813 ± 191 | −16%; p = 0.01 | Reference 2 |
| | BSA-AGE and *Albizia Julibrissin* extract | 944 ± 59 | — | +16%; p < 0.05 |

*Activity of the proteasome in $\Delta UA/min/10^6$ cells c. Reduction in Formation of AGE-Pigments Principle and protocol: MGO is indirectly involved in the production of another group of toxins called lipofuscin. This pigment, which is seen on skin sections, is yellow in colour. It is poorly characterised as it is formed from an aggregate of different damaged cell components. Reduced functioning of the proteasome allows it to accumulate. Glycation (and therefore alteration) of the proteasome promotes the accumulation of this toxic pigment.

The same "fatiguing" cell stress as above in point 2a was used, alternating two rest periods (+/− of *Albizia Julibrissin* extract) and 2 periods of stress (+/− the *Albizia Julibrissin* extract with 500 μM microns of MGO). At the end of the second glycating stress, a dosage of the lipofuscin marker, the dityrosine was performed on the cell and reduced to the number of cells.

Results: The results show that MGO produces a large rise in dityrosine accumulation (+129%, p<0.01). In parallel, the *Albizia Julibrissin* extract significantly restricted its formation.

The extract of *Albizia Julibrissin* possessing the ability to basally reduce dityrosine formation (undetectable in our experiments for this case), the amount of dityrosine observed with MGO in the presence of the extract is less than the negative control (without MGO).

TABLE 9

Change in the accumulation of the Lipofuscine AGE-pigment.

| | | Dityrosine (AFU*/$10^6$ cell.) | % Change; significance | |
|---|---|---|---|---|
| Fibroblasts; n = 3 | Control without MGO | 3.58 ± 2.91 | Reference 1 | — |
| | Control with MGO | 8.16 ± 5.09 | +129%; p < 0.01 | Reference 2 |
| | MGO and *Albizia Julibrissin* extract | 1.63 ± 1.70 | — | −81%; p < 0.01 |

*AFU: Arbitrary fluorescence unit; positive MGO control: Trolox 500 μM: −61.1% (p < 0.01)

d. Reduction in Effects of AGEs on Vascularisation

Principle and protocol: The AGEs are formed in the direct environment of vessels or in the vessels themselves, which may lead to the accumulation of waste and fluids causing the dark colour of under eye circles. The Het-CAM uses eggs at a very early stage in their development, with the nervous system not yet being fully developed. An original method was developed by the inventors to assess the AGE-related changes in vascularisation.

BSA was glycated with MGO. At the end of this phase, this glycotoxins (glycated BSA) was placed in contact for a—days with or without the *Albizia Julibrissin* extract.

Both types of glycating solutions were then applied to the egg membrane. Blood vessels which had been invisible until that point became clearly visible as a result of vasodilatation induced by the AGEs. Results were scored to assess the reduction in negative effects on the vessels.

Results

TABLE 10

Reduction in the negative AGE-related effects by an extract of *Albizia Julibrissin* in an Het-CAM test

| | Concentration | Sum of scores | % Change; significance | |
|---|---|---|---|---|
| n = 4 | BSA control | 2.0 ± 2.45 | Reference 1 | — |
| | BSA-AGE control | 9.5 ± 1.91 | +375%; p < 0.01 | Reference 2 |
| | BSA-AGE and 0.075% of the *Albizia Julibrissin* extract | 4.3 ± 2.06 | | −55%; p < 0.01 |
| | BSA-AGE and 0.225% of the *Albizia Julibrissin* extract | 2.8 ± 1.50 | | −70%; p < 0.01 |

After applying BSA-AGE to the egg vascular network, its toxic effect is expressed rapidly and severe damage is seen with blood leakage and development of the vascular network.

Application of BSA detoxified (deglycated) with the *Albizia Julibrissin* extract produced a large dose-dependent reduction in damage: −55% at 0.075% of the extract (p<0.01) and −70% at 0.225% of the extract (p<0.01). The *Albizia Julibrissin* extract therefore helps to protect the vascular network from deleterious damages of glycotoxins, reduces the blood leakages and excess vascularisation, and therefore the color of dark circles, compared to control.

e. Conservation of Fibroblast Melatonin Synthesis

Principle and protocol: As mentioned before, melatonin has often emphasized an interest in cell protection. Changes in human dermal fibroblasts (HDF) melatonin synthesis in the presence or absence of methylglyoxal (MGO) were monitored. A dose-dependent reduction of up to −20% in melatonin due to this stress after contact for 2 hours was thus demonstrated.

In a second series of experiments, HDF have been in contact with the extract according to the invention for 24 hours, then after rinsing have been in contact with MGO as before. Melatonin synthesis was monitored after 24 hours.
Results

TABLE 11

Change in melatonin synthesis due to glycating stress;
effect of the *Albizia Julibrissin* extract of the invention

| | Concentration | Melatonin (pg/ml/10⁶cell.) | % Change; significance | |
|---|---|---|---|---|
| n = 4 | Control without MGO | 276 ± 38 | Reference 1 | — |
| | 0.08% of the *Albizia Julibrissin* extract | 238 ± 26 | −14%; dns | — |
| | Control MGO | 188 ± 8 | −32%; p < 0.05 | Reference 2 |
| | 0.08% of the *Albizia Julibrissin* extract and MGO | 260 ± 12 | — | +38%; p < 0.01 |

MGO produced a 32% fall in melatonin (p<0.05) compared to the control; the extract according to the invention, used in prevention, maintained melatonin at steady state concentrations and prevented its depletion.

D) In Vitro Tests: Activity of the Combination of an *Albizia Julibrissin* Extract and Darutoside 1. Increase of the Expression of 3 Gerontogenes The term gerontogene deal with all genes presenting a change in their activity during the aging process or who thanks to their function plays a role in maintaining homeostasis.

a) FOXOs (Forkhead Transcription Factor Class O)

Forkhead transcriptions factors class O is implicated in the regulation of oxidative damages. When deacetylated, FOXOs proteins are more active. Cellular stress results in their acetylation and a decrease activity. Sirtuin (SIRT1) is one of the main activators of the FOXOs pathway. FOXO3a gene extinction in human dermal fibroblasts has similarities with the senescent phenotype: a greater production of ROS (reactive oxygen species) and a population doubling time more important.

b) Sestrins (Sesns)

Sestrins are stress response proteins. They suppress oxidative damages, acting directly like antioxidant, or like autophagy inductor, allowing elimination of defective mitochondria, ROS producer. So, they are considered as physiological brakes in the process of aging.

SIPS (Stress Induced Premature Senescence) protocol was used to test the effect of the combination of the invention.

Human dermal fibroblasts are cultured for 3 days. Then they received or not the product of the invention (test product) to be tested at different concentration for another 3 days period. Cells are then subjected to an oxidative stress ($H_2O_2$) during 2 hours. Cell monolayers are again contacting or not with the test product for 6 hours. Next, RNA are extracted and the expression of 3 gerontogens is quantified by real time RT-PCR.

Cells treated with the combination of the invention are compared to untreated cells.

TABLE 12

| | FOXO3a | | SESN1 | | SIRT1 | |
|---|---|---|---|---|---|---|
| Tested Product | Ratio* | stat | Ratio* | Stat | Ratio* | stat |
| 5 ppm Darutoside + 5 ppm *Albizia Julibrissin* extract | 2.75 | p < 0.01 | 1.70 | dns | 1.65 | p < 0.01 |
| 15 ppm Darutoside + 15 ppm *Albizia Julibrissin* extract | 2.81 | p < 0.01 | 2.50 | p < 0.01 | 1.62 | p < 0.01 |

Ratio = 1 for the control

The above results show a significant induction of these 3 gerontogens with the combination of the invention, compared to untreated cells.

2. Non Enzymatic Glycation of Elastin

Non-enzymatic glycation occurring between a protein and a reducing sugar like fructose or glucose is a spontaneous and slow reaction that can be accelerated by heat. In this test, the protein is soluble bovine elastin and the reducing sugar is fructose. They are incubated with or without test products at 50° C. for 9 days. Final products resulting from glycation may be quantified by fluorescence ($\lambda ex=360$ nm and $\lambda em=460$ nm).

TABLE 13

| Tested product | Concentration | Glycation (UFA) | % change vs. control |
|---|---|---|---|
| Control | | 6096 +/− 438 | Reference |
| Darutoside | 15 ppm | 5843 +/− 383 | −4%; dns |

TABLE 13-continued

| Tested product | Concentration | Glycation (UFA) | % change vs. control |
|---|---|---|---|
| Albizia Julibrissin extract | 15 ppm | 4670 +/− 342 | −23%; p < 0.05 |
| Combination of the invention | 15 ppm Darutoside + 15 ppm Albizia Julibrissin extract | 4210 +/− 223 | −31%; p < 0.01 |

Aminoguanidine 0.03%: −99%; p < 0.01

The above results show a decrease in elastin non-enzymatic glycation with the Albizia Julibrissin extract compared to the control (−23%; p<0.05). While Darutoside has alone no effect, the combination of the Albizia Julibrissin extract with Darutoside show a synergistic effect (−31%; p<0.01).

3. An Inhibitory Activity of Metalloproteinases MMP1 and MMP2

Human dermal fibroblasts are cultured until confluence. Then cells are contacted with or without the test products during 24 hours. Then cells are stressed with an extract of cigarette smoke with or without the test products. After a last incubation with or without the test products, metallo-proteinases MMP1 and MMP2 present in the culture media are measured by ELISA and reduced to the number of cells (evaluated with the Hoescht reagent).

TABLE 14

| Test product | Concentration | % change vs. control |
|---|---|---|
| | MMP1 ($ng/10^6$ cells) | |
| Control without stress | 882 +/− 100 | |
| Control stress | 9200 +/− 1590 | Reference |
| Combination of the invention | 10 ppm Darutoside + 10 ppm Albizia Julibrissin extract | 7355 +/− 889 | −20%; dns |
| | 15 ppm Darutoside + 15 ppm Albizia Julibrissin extract | 6141 +/− 393 | −33%; p < 0.01 |
| Trolox | 500 μM | 3962 +/− 759 | −57%; p < 0.05 |
| | MMP2 ($ng/10^6$ cells) +/− SD | |
| Control without stress | 161 +/− 26 | |
| Control stress | 407 +/− 82 | Reference |
| Combination of the invention | 5 ppm Darutoside + 5 ppm Albizia Julibrissin extract | 224 +/− 46 | −45%; p < 0.01 |

These results show an increase of MMP after the stress. In treated cells, the combination of the invention leads to a decrease of the MMP induced by the stress, compared to the control cells.

4. an Increase of Collagen I in Human Dermal Fibroblasts

Human dermal fibroblasts are cultured during 24 hours. Then cells are contacted with or without the test products during 6 days. Collagen I produced by cells is finally quantified by immunolabeling of fixed cell layers.

TABLE 15

| Test product | Concentration | % change vs. control |
|---|---|---|
| Combination of the invention | 5 ppm Darutoside + 5 ppm Albizia Julibrissin extract | +111% (p < 0.01) |
| | 10 ppm Darutoside + 10 ppm Albizia Julibrissin extract | +89% (p < 0.01) |

The combination of the invention stimulates the collagen I synthesis in treated cells compared to control cells.

E) Examples of Galenic Formulations

Active ingredient of the invention: composition comprising an extract of Albizia Julibrissin prepared according to paragraph B.

Various formulations are described below, with or without additional cosmetic active ingredients, the latter coming for each case in support and/or complement of the activity of the active ingredient according to the invention. These ingredients can be of any class according to their(s) function(s), site of application (body, face, neck, chest, hands, etc.), the desired end effect and the target consumer.

EXAMPLE 1

Cream Form

| Ingredients | INCI names | Day cream Weight % | Night cream Weight % |
|---|---|---|---|
| Phase A | | | |
| $H_2O$ | Water | Qsp 100 | Qsp 100 |
| Ultrez 10 | Carbomer | 0.25 | 0.25 |
| Phase B | | | |
| Glycerin | Glycerin | 4.00 | 4.00 |
| Phenoxyethanol | Phenoxyethanol | qs | qs |
| Phase C | | | |
| Brij S2 SS | Steareth-2 | 0.40 | 0.40 |
| Brij S10 SO | Steareth-10 | 1.20 | 1.20 |
| Crodafos CES | Cetearyl alcohol & Dicetyl phosphate & Ceteth 10 phosphate | 4.00 | 4.00 |
| Crodacol CS 90 | Cetearyl Alcohol | 1.50 | 1.50 |
| Laurocapram | Laurocapram | 2.50 | 2.50 |
| BRB CM 56 | Cyclopentasiloxane (and) Cyclohexasiloxane | 2.00 | 2.00 |
| Crodamol OSU | Diethylhexyl succinate | 7.00 | 7.00 |
| Phase D | | | |
| Potassium sorbate | Potassium Sorbate | 0.10 | 0.10 |
| Phase E | | | |
| $H_2O$ | Water | 3.00 | 3.00 |
| NaOH 30% | Sodium Hydroxide | 0.40 | 0.40 |
| Phase F | | | |
| Active ingredient of the invention | | 2.00 | 4.00 |

Procedure: Weigh phase A and let swallow without stirring for 30 min. Put phase A to heating at 75° C. in a water bath. Weigh and mix phase B. Weigh phase C and heat to 75° C. in a water bath, mix thoroughly. Add phase B to phase A. Mix well. Under stirring pour phase C into phase A+B. Mix thoroughly. Add phase D, extemporaneously. Add phase E, mix thoroughly. Add phase F, mix thoroughly.

EXAMPLE 2

Night Balm Form

| Ingredients | INCI names | Weight % |
|---|---|---|
| Phase A | | |
| H₂O | Water | Qsp 100 |
| Benzoate de sodium | Sodium Benzoate | qs |
| Sorbate de potassium | Potassium Sorbate | qs |
| Glycerin | Glycerin | 3.70 |
| Magnesium sulfate | Magnesium Sulfate | 0.70 |
| Phase B | | |
| Unsaponifiable shea butter | Shea Butter | 0.50 |
| Arlacel 986 | Sorbitan Isostearate & Hydrogenated Castor Oil & Cera Alba & Stearic Acid | 9.00 |
| Syncrowax HRC | Tribehenin | 2.00 |
| Magnesium stearate | Magnesium Stearate | 1.00 |
| Pripure 3759 | Squalane | 10.00 |
| Sweet almond oil | *Prunus Amygdalus Dulcis* Oil | 4.00 |
| Crodamol GTCC | Caprylic/Capric Triglyceride | 5.00 |
| Covi-Ox T90 | Tocopherol | 0.10 |
| Argan oil | *Argania Spinosa* Kemel Oil | 1.00 |
| Phase C | | |
| Active ingredient of the invention | | 3.00 |
| Phase D | | |
| Perfume | Fragrance | 0.20 |

Procedure: Weigh phase A and heat in a water bath at 85° C. Weigh phase B and heat in a water bath at 85° C. Weigh phase C. Prior to forming the emulsion, add phase C to phase A, mix thoroughly. Slowly add phase A+C into phase B under vigorous stirring. Mix thoroughly under stirring to cool. Add phase D in the emulsion around 35° C., mix thoroughly.

Examples of additional ingredients that can be added to this formulation:

Covi-Ox T90™: antioxidant active (tocopherol) marketed by Cognis. For example 0.1% can be added to phase B.

Crodarom Goji™: anti-oxidant, detoxifying and moisturizer active marketed by Crodarom. It may be added at the same time as the phase C to phase A, for example up to 2.50%.

EXAMPLE 3

Aftershave Emulsion Form (Gel-Cream)

| Ingredients | INCI names | Weight % |
|---|---|---|
| Phase A | | |
| H₂O | Water | Qsp 100 |
| Sodium benzoate | Sodium Benzoate | qs |
| Potassium sorbate | Potassium Sorbate | qs |
| Phase B | | |
| Glycerin | Glycerin | 5.00 |
| Keltrol CG-SFT | Xanthan Gum | 1.00 |
| Crodesta F-50 | Sucrose Distearate | 0.90 |
| Crodesta F-160 | Sucrose Stearate | 0.30 |
| Phase C | | |
| Crodamol GTCC | Caprylic/Capric Triglyceride | 3.00 |
| Prisorine 3505 | Isostearic Acid | 5.00 |
| Phase D | | |
| Alcool | Ethanol | 10.00 |
| Menthol Cristal | Menthol | 0.05 |
| Phase E | | |
| H₂O | Water | 0.10 |
| Lactic acid | Lactic Acid | 0.10 |
| Phase F | | |
| Active ingredient of the invention | | 3.00 |
| Phase G | | |
| Perfume | Fragrance | 0.10 |

Procedure: Weigh phase A and put it under propeller stirring. Weigh and mix phase B. Add phase B to phase A under stirring, homogenize thoroughly for 30 minutes. Heat phase A+B at 75° C. in a water bath. Weigh phase C and heat to 75° C. in a water bath. Pour phase C into phase A+B under Staro stirring, mix thoroughly. Weigh and homogenized phase D. Add phase D in the previous phase, around 40° C., mix thoroughly. Adjust pH to 5.00-5.50 with phase E, below 35° C., mix thoroughly. Add phase F, mix well. Add phase G, mix well. Check pH at 5.50-5.00.

Examples of additional ingredients that can be added to this formulation:

Kelisoft™: anti-hair regrowth active marketed by Sederma. It can be added at the end of the formulation before phase G up to 3.00%.

Calmosensine™: soothing active for sensitive skins marketed by Sederma. It can be added at the end of the formulation before phase G up to 3.00%.

NG Seve de Bouleau™: toning and moisturizing agent marketed by Sederma. It can be added at the end of the formulation before phase G up to 3.00%.

EXAMPLE 4

Gel Form for Eye Contour

| Ingredients | INCI names | Weight % |
|---|---|---|
| Phase A | | |
| H₂O | Water | Qsp 100 |
| Potassium sorbate | Potassium Sorbate | qs |
| Benzoate de Sodium | Sodium Benzoate | qs |
| Phase B | | |
| Butylene Glycol Vegetal | Butylene Glycol | 5.00 |
| Keltrol CG-SFT | Xanthan Gum | 0.60 |
| Kelcogel CG-HA | Gellan Gum | 0.20 |
| Phase C | | |
| Natragem S140 | Polyglyceryl-4 Laurate/Sebacate (and) Polyglyceryl-6 Caprylate/Caprate (and) Aqua | 3.00 |
| Pripure 3759 | Squalane Vegetal | 1.00 |
| Phase D | | |
| H₂O | Water | 0.05 |
| Lactic acid | Lactic Acid | 0.05 |

-continued

| Ingredients | INCI names | Weight % |
|---|---|---|
| Phase E | | |
| Active ingredient of the invention | | 3.00 |
| Phase F | | |
| Perfume | Fragrance | 0.10 |

Procedure: Weigh and homogenize phase A. Weigh phase B and mix homogenously. Add phase B into phase A under propeller stirring. Let swallow. Weigh phase C, homogenize. Add phase C into phase A+B under strong helix stirring. Leave it to homogenize for 1 hour under normal propeller stirring. Adjust to pH 5.50 with phase D. Homogenize under propeller stirring. Add phase E in the previous phase, mix thoroughly. Add phase F, mix thoroughly.

Examples of additional ingredients that can be added to this formulation:

EYELISS™: eye contour active (especially for dark circles and under eye bags) marketed by Sederma. 3.00% can be added to phase E.

EXAMPLE 5

Mask Form

| Ingredients | INCI names | Weight % |
|---|---|---|
| Phase A | | |
| H₂O | Water | Qsp 100 |
| Sodium benzoate | Sodium benzoate | qs |
| Potassium sorbate | Potassium Sorbate | qs |
| Phase B | | |
| Zemea | Propandiol | 10.00 |
| Glycerin Bio | Glycerin | 10.00 |
| Kelcogel CG HA | Gellan Gum | 0.50 |
| Jaguar S | Guar Gum | 0.60 |
| Phase C | | |
| Alcool | Ethanol | 5.00 |
| Phase D | | |
| H₂O | Water | 1.00 |
| Lactic acid | Lactic acid | 0.10 |
| Phase E | | |
| Active ingredient of the invention | | 3.00 |
| Phase F | | |
| Perfume | Fragrance | 0.10 |

Procedure: Weigh phase A and put it under propeller stirring. Weigh and mix phase B. Slowly add phase B into phase A under propeller stirring, mix thoroughly. Heat phase A+B in a water bath at 80° C. without stirring for 2h. Stir quickly, then let cool under stirring. Add phase C to the previous phase, around 40° C. Adjust the pH to 5.50 with phase D, below 35° C. mix thoroughly. Add phase E, under slow stirring. Add phase F, mix thoroughly. Add phase G, mix thoroughly. Check the pH at 5.0-5.5.

Examples of additional ingredients that can be added to this formulation:

KOMBUCHKA™: active acting on the radiance of complexion, marketed by Sederma. 3.00% may be added at the end of the formulation before phase F.

Novaplant Ginger Special™: active increasing blood circulation marketed by Crodarom. 2.00% diluted in Crodateric CAB 30 (Cocamidopopyl Betaine) may be added after phase D.

EXAMPLE 6

Gel Form for Face

| Ingredients | INCI names | Weight % |
|---|---|---|
| Phase A | | |
| H₂O | Water | Qsp 100 |
| Cetyl hydroxyethylcellulose | Cetyl hydroxyethylcellulose | 0.30 |
| Phase B | | |
| Ultrez 10 | Carbomer | 0.40 |
| H₂O | Water | 20.00 |
| Phase C | | |
| Glycerin | Glycerin | 3.00 |
| Panstat | Ethyl & Methyl & Propyl parabens | 0.30 |
| Phase D | | |
| Marcol 82 | Mineral oil | 4.00 |
| Crillet 1 | Polysorbate 20 | 1.00 |
| Crodamol AB | C12-15 Alkyl Benzoate | 2.00 |
| Pemulen TR2 | C10-30 Alkyl Acrylate cross polymer | 0.30 |
| Phase E | | |
| Potassium sorbate | Potassium Sorbate | 0.10 |
| Phase F | | |
| H₂O | Water | 5.00 |
| NaOH 10N | Sodium Hydroxide | 0.50 |
| Phase G | | |
| Active ingredient of the invention | | 3.00 |

Procedure: Disperse phase A under stirring. Sprinkle Ultrez 10 in water, let swallow 30 minutes. Heat phase C until complete dissolution. Mix phase A to phase B. Add C in phase (B+A). Add phase D under stirring, in the phase (A+B+C). Add phase E. Neutralize with phase F. Add phase G and mix.

Examples of additional ingredients that can be added to this formulation:

RIGIN™: active marketed by Sederma improving elasticity and firmness of the skin, increasing hydration and smoothing the skin. 3% by weight can be added for example in phase G.

MATRIXYL 3000™: peptide-based anti-wrinkle ingredient marketed by Sederma which helps repairing skin damages caused by aging. 3% by weight can be added for example in phase G.

MATRIXYL synthe'6™: peptide-based anti-wrinkle ingredient marketed by Sederma which helps repairing skin damages caused by aging. 2% by weight can be added for example to phase G.

EXAMPLE 7

Other Cream Form

| Ingredients | INCI names | Weight % |
| --- | --- | --- |
| Phase A | | |
| H₂O | Water | Qsp 100 |
| Ultrez 10 | Carbomer | 0.40 |
| Phase B | | |
| Glycerin | Glycerin | 3.00 |
| Panstat | Ethyl & Methyl & Propyl parabens | 0.30 |
| Phase C | | |
| Polawax GP 200 | Cetearyl Alcohol & polysorbate 20 | 1.00 |
| Crodacol CS 90 | Cetearyl Alcohol | 1.00 |
| Crodamol STS | PPG-3 Benzyl Ether Myristate | 1.00 |
| DC 200 5 cps | Dimethicone | 2.50 |
| Crodamol TN | Isotridecyl Isononanoate | 5.00 |
| Phase D | | |
| Potassium sorbate | Potassium sorbate | 0.10 |
| Phase E | | |
| NaOH 30% | Sodium hydroxide | 0.40 |
| H₂O | Water | 4.00 |
| Phase F | | |
| Active ingredient of the invention | | 2.00 |
| Phase G | | |
| Perfume | Fragrance | 0.10 |

Procedure: Weigh phase A and let swallow for 30 minutes. Then heat phase A in a water bath at 75° C. Heat phase B until dissolved. Add phase B to phase A. Heat phase C in a water bath at 75° C. Under stirring, add phase C to phase (A+B). Add phase thoroughly. Neutralize with phase E to 55° C. Add phase F, then phase G, homogenize thoroughly.

Examples of additional ingredients that can be added to this formulation:

DERMAXYL™: anti-aging active marketed by Sederma that smoothes wrinkles and repair the skin barrier. 2% by weight can be added for example to phase (A+B+C).

Retinol, Resveratrol et Niacinamide: anti-aging ingredients, in particular anti-wrinkle agents. 0.1% of retinol or 0.5% of resveratrol may for example be added to phase (A+B+C). 10% of niacinamide in water can be added for example to phase F.

CHRONODYN™: active marketed by Sederma that tones and firms the skin, erases signs of fatigue. 3% can be added for example to phase F.

VENUCEANE™: active marketed by Sederma that prevents visible signs of photo-aging (spots, wrinkles, dryness . . . ), protects cell structures from damages caused by UV and strengthens skin integrity. 3% can be added for example to phase F.

EXAMPLE 8

Cream Form for Body

| Ingredients | INCI names | Weight % |
| --- | --- | --- |
| Phase A | | |
| H₂O | Water | qsp 100 |
| Ultrez 10 | Carbomer | 0.40 |
| Phase B | | |
| Glycerin | Glycerin | 3.00 |
| Panstat | Ethyl & Methyl & Propyl parabens | 0.30 |
| Phase C | | |
| Crill 3 | Sorbitan Stearate | 2.00 |
| Marcol 82 | Mineral oil | 4.00 |
| Cromollient DP3A | PPG 3 Myristyl Ether Adipate | 1.00 |
| Cithrol GMS AS | Glyceryl stearate & PEG 100 stearate | 3.00 |
| Phase D | | |
| Potassium sorbate | Sorbate de potassium | 0.10 |
| Phase E | | |
| NaOH 30% | Sodium hydroxide | 0.40 |
| H₂O | Water | 4.00 |
| Phase F | | |
| Active ingredient of the invention | | 3.00 |
| Phase G | | |
| Perfume | Fragrance | 0.10 |

Procedure: Weigh phase A and let swallow for 30 minutes. Heat phase A in a water bath at 75° C. Heat phase B until dissolved. Add phase B to phase A. Heat phase C in a water bath at 75° C. Under stirring, add phase C to phase (A+B). Add phase D, mix thoroughly. Neutralize with phase E around 55° C., mix well. Add phase F and phase G, mix thoroughly.

Examples of additional ingredients that can be added to this formulation:

JUVINITY™: active marketed by Sederma which reduces the signs of aging on the face and "decolleté", smooth wrinkles, restructures and densities the dermis. 2% can be added for example to phase (A+B+C).

Tocopherol (vitamin E) or u α-lipoic acid (ALA): active with anti-oxidant and anti-radical properties. 0.5% by weight may be added for example to phase (A+B+C).

O.D.A. White™: active marketed by Sederma who lightens the skin by reducing the synthesis of melanin. 1% can be added for example to phase (A+B+C).

Bio-Bustyl™: active marketed by Sederma comprising peptides and a bacterial filtrate having a global action on firmness and tone on the bust. 3% can be added for example to phase F.

EXAMPLE 9

Serum Form

| Ingredients | INCI names | Weight % |
|---|---|---|
| Phase A | | |
| Optasens G 40 | Carbomer | 0.25 |
| H$_2$O | Water | Qsp 100 |
| Phase B | | |
| Butylene Glycol | Butylene Glycol | 3.00 |
| Phenoxyethanol | Phenoxyethanol | 0.20 |
| Phase C | | |
| Crillet 1 | Polysorbate 20 | 0.50 |
| DC 245 | Cyclopentasiloxane | 1.00 |
| Crodamol CAP | Cetearyl Ethylhexanoate | 2.00 |
| Crodamol STS | PPG-3 Benzyl Ether Myristate | 0.50 |
| Pemulen TR2 | Acrylates/C 10-30 Alkyl Acrylates cross polymer | 0.20 |
| Phase D | | |
| Potassium sorbate | Potassium Sorbate | 0.10 |
| Phase E | | |
| H$_2$O | Water | 4.00 |
| NaOH 30% | Sodium Hydroxiide | 0.45 |
| Phase F | | |
| Active ingredient of the invention | | 3.00 |
| Phase G | | |
| Perfume | Fragrance | 0.10 |

Procedure: Phase A: sprinkle carbomer in water, let stand 15 minutes. Mix phase B. Pour phase B in phase A, homogenize. Weigh phase C, mix and add in phase A+B under stirring. Let swallow 1 hour. Extemporaneously add phase D in the previous phase under stirring. Neutralize with phase E. Start stirring. Then add phase F. Allow to mix at least 1 hour under stirring then add phase G. Mix well.

Examples of additional ingredients that can be added to this formulation:

LUMISPHERE™: active marketed by Sederma which is a combination of diacetylboldine (DAB) encapsulated in microcapsules of polymethylmethacrylate and modified titanium dioxide manganese (TiO$_2$Mn). The TiO$_2$Mn gives the skin a unifying and luminous mattifying effect and DAB provides a lightening physiological effect. 4% may for example be added to phase F.

REVIDRATE™: active marketed by Sederma that in particular improves cohesion and hydration of the epidermis. 2% may be added for example to phase C.

EVERMAT™: active marketed by Sederma, which decreases the secretion of sebum and thus participates in the treatment of oily skin 4% may for example be added to phase F.

HALOXYL™: active marketed by Sederma, which improves the eye contour by resorbing eye rings. 3% can be added for example to phase F.

EXAMPLE 10

Lotion Form

| Ingredients | INCI names | Weight % |
|---|---|---|
| Phase A | | |
| H$_2$O | Water | Qsp 100 |
| Phase B | | |
| Butylene Glycol | Butylene Glycol | 5.00 |
| Phenoxyethanol | Phenoxyethanol | 0.20 |
| Phase C | | |
| Crillet 1 | Polysorbate 20 | 2.00 |
| Crodamol STS | PPG-3 Benzyl Ether Myristate | 0.10 |
| Phase D | | |
| Potassium sorbate | Potassium Sorbate | 0.10 |
| Phase E | | |
| Active ingredient of the invention | | 3.00 |
| Phase F | | |
| Perfume | Fragrance | 0.10 |

Procedure: Weigh phase A. Weigh phase B and mix. Add phase B into phase A under stirring for 30 minutes. Weigh phase C, mix until obtaining a homogenous blend. Add phase C into phase A+B under stirring. Add phase D in the previous phase. Add phase E under stirring, homogenize well. Weigh phase F, mix and add to the previous phase, homogenize thoroughly.

Examples of additional ingredients that can be added to this formulation:

EYELISS™: as mentioned above. 3.00% can be added for example to phase E.

Ac-Net™: active marketed by Sederma offering a complete treatment for oily and acne prone skins. 3% can be added for example to phase E.

EVERMAT™: as mentioned above. 4% can be added for example to phase E.

HYDRERGY™: active marketed by Sederma which is a long term moisturizing agent and which stimulates the synthesis of ATP. 3% may be added for example to phase E.

EXAMPLE 11

Capillary Lotion

| Ingredients | INCI names | Weight % |
|---|---|---|
| Phase A | | |
| Incroquat CTC 30 | Cetrimonium chloride | 1.00 |
| Citric acid | Citric Acid | 0.22 |
| Trisodium citrate | Citrate trisodique | 1.20 |
| Sorbate | Potassium Sorbate | 0.10 |
| H$_2$O | | Qsp |
| Phase B | | |
| Nipagine | Methyl paraben | 0.20 |
| Procetyl AWS | PPG 5 Ceteth 20 | 2.00 |
| Phase C | | |
| Active ingredient of the invention | | 3.00 |

EXAMPLE 12

Lip Balm

| Ingredients | INCI names | Weight % |
|---|---|---|
| Phase A | | |
| H₂O | | qsp 100% |
| Potassium sorbate | Potassium Sorbate | 0.10 |
| Magnesium sulfate | Magnesium Sulfate | 0.70 |
| Phase B | | |
| Abil EM 90 | Cetyl Dimethicone Copolyol | 3.00 |
| Methyl Paraben | Methyl Paraben | 1.00 |
| Syncrowax HRC | Tribehenin | 0.30 |
| Crodamol STS | PPG-3 Benzyl Ether Myristate | 2.00 |
| Mineral Oil | Mineral Oil | 19.00 |
| Phase C | | |
| Active ingredient of the invention | | 1.00 |
| Phase D | | |
| Perfume | Fragrance | 0.10 |

| Ingredients | INCI names | Weight % |
|---|---|---|
| Phase D | | |
| Crillet 1 | Polysorbate 20 | 1.00 |
| Perfume | Fragrance | 0.10 |

Procedure: Heat phase A at 85° C. Mix phase B and heat at 85° C. Mix. Slowly pour phase A in phase B under stirring (Staro s=3000, then s=1200). Add phase C preheated at 80° C., homogenize. Add phase D around 35° C. Cast.

F) Specific Examples of Galenic Formulations for the Combination According to the Invention of an Extract of *Albizia Julibrissin* and Darutoside Active ingredient of the invention: composition comprising an extract of *Albizia Julibrissin* and Darutoside prepared according to paragraph B.

Various formulations are described below, with or without additional cosmetic active ingredients, the latter coming for each case in support and/or complement of the activity of the active ingredient according to the invention. These ingredients can be of any class according to their(s) function(s), site of application (body, face, neck, chest, hands, etc.), the desired end effect and the target consumer.

EXAMPLE 13

Cream Form, in Particular for Eye Contour

| Ingredients | INCI names | Weight % |
|---|---|---|
| Phase A | | |
| H₂O | Water | Qsp 100 |
| Optasense G83 | Carbomer | 0.30 |
| Phase B | | |
| Glycerine | Glycerin | 3.00 |
| Natrosol 250M | Hydroxyethyl Cellulose | 0.20 |
| Phenoxyethanol | Phenoxyethanol | 1.00 |
| Phase C | | |
| Crodamol CSO-LQ-(LK) | Cetearyl Ethylhexanoate | 6.00 |
| Optasense G82 | Acrylates/C10-30 Alkyl Acrylate Crosspolymer | 0.20 |
| Phase D | | |
| Potassium sorbate | Potassium Sorbate | 0.10 |
| Phase E | | |
| H₂O | Water | 5.50 |
| NaOH 30% | Sodium Hydroxide | 0.55 |
| Phase F | | |
| Tween 20-LQ-(RB) | Polysorbate 20 | 0.50 |
| Fragrance | Fragrance | 0.10 |
| Phase G | | |
| Ingredient of the invention | — | 3.00 |

Procedure:

Sprinkle phase A in water without stirring, let stand 1 hour. Homogenize phase B and add it to into phase A under propeller stirring for 30 minutes. Add phase C into phase A+B under staro stirring. Add phase D extemporaneously in the previous phase under staro with stirring. Neutralize with phase E under staro stirring. Mix phase F and add it in the previous phase under staro stirring. Add phase G in the previous phase, homogenize well.

Examples of additional ingredients that can be added to this formulation:

MATRIXYL 3000™: peptide-based anti-wrinkle ingredient marketed by Sederma which helps repairing skin damages caused by aging. 3% by weight can be added for example at the end of the formulation.

RESISTEM™: anti-age ingredient marketed by Sederma which is a plant extract obtained by stem cell culture of *Globularia cordifolia*. It helps reduce the level of pro-ageing agents and local micro-inflammation, decreases skin redness and enhances natural skin glow. 3% by weight can be added for example at the end of the formulation.

EXAMPLE 14

Gel Form, in Particular for Eye Contour

| Ingredients | INCI names | Weight % |
|---|---|---|
| Phase A | | |
| H₂O | Water | 33.00 |
| Optasense G83 | Carbomer | 0.30 |
| Phase B | | |
| H₂O | Water | Qsp 100 |
| PVP K30 | PVP | 0.20 |
| Phase C | | |
| Hydrolite 5 | Pentylene Glycol | 5.00 |
| Phenoxyethanol | Phenoxyethanol | Qs |
| Satiagel VPC 614 | *Chondrus Crispus* (Carrageenan) Extract | 0.25 |
| N-Hance HP40 | Hydroxypropyl Guar | 0.25 |

-continued

| Ingredients | INCI names | Weight % |
|---|---|---|
| Phase D | | |
| Potassium sorbate | Potassium Sorbate | 0.10 |
| Phase E | | |
| H₂O | Water | 3.00 |
| NaOH 30% | Sodium Hydroxide | 0.30 |
| Phase F | | |
| Ingredient of the invention | | 3.00 |
| Phase G | | |
| Fragrance | Fragrance | 0.10 |

Procedure: Sprinkle phase A in water and let stand 1 hour without stirring. Spread phase B in water under with rapid propeller stirring, let mix 30 minutes. Weigh and homogenize phase C. Add phase C into phase B under propeller stirring. Let stand 30 minutes. Add phase A into phase B+C under blade stirring. Add phase D in the previous phase under propeller stirring and then blade stirring. Neutralize the previous phase with phase F under blade stirring. Add phase G in the previous phase, mix well.

Examples of additional ingredients that can be added to this formulation:

IDEALIFT™: a lipopeptide based ingredient marketed by Sederma that fights against skin sagging and improves resistance to gravity. 4% can be added at the end of the formulation.

EXAMPLE 15

Serum Form

| Ingredients | INCI names | Weight % |
|---|---|---|
| Phase A | | |
| H₂O | Water | Qsp 100 |
| Phase B | | |
| Glycerin | Glycerin | 5.00 |
| Phenoxyethanol | Phenoxyethanol | Qs |
| Crovol A70 | PEG-60 Almond Glycerides | 0.50 |
| Phase C | | |
| Dimethicone 5 cs | Dimethicone 5 cs | 2.50 |
| Crodamol AB-LQ-(RB) | C12-15 Alkyl Benzoate | 4.50 |
| Crodamol GTEH-LQ-(MV) | Triethylhexanoin | 2.50 |
| Crodamol CSO-LQ-(LK) | Cetearyl Ethylhexanoate | 3.00 |
| Fragrance | Fragrance | 0.10 |
| Optasense G82 | Acrylates/C10-30 Alkyl Acrylate Crosspolymer | 0.20 |
| Phase D | | |
| Potassium sorbate | Potassium Sorbate | 0.10 |
| Phase E | | |
| H₂O | Water | 1.70 |
| NaOH 30% | Sodium Hydroxide | 0.17 |
| Phase F | | |
| Ingredient of the invention | | 3.00 |

Procedure: Weigh phase A and put it under propeller stirring. Weigh and homogenize phase B. Add phase B into phase A, mix well. Weigh phase C, mix well. Add phase C into phase A+B under propeller stirring. Extemporaneously add phase D under propeller stirring. Add phase E, leave 30 minutes for homogeneisation under blade stirring.

Example of additional ingredients that can be added to this formulation:

RIGIN™: active marketed by Sederma improving elasticity and firmness of the skin, increasing hydration and smoothing the skin. 3% by weight can be added at the end of the formulation.

EXAMPLE 16

Cleansing Lotion

| Ingredients | INCI names | Weight % |
|---|---|---|
| Phase A | | |
| H₂O | Water | Qsp 100 |
| Potassium sorbate | Potassium Sorbate | 0.10 |
| Phase B | | |
| Butylene Glycol | Butylene Glycol | 35.00 |
| Crovol A70-LQ-(RB) | PEG-60 Almond Glycerides | 1.00 |
| Crodateric CAB 30-LQ-(RB) | Cocamidopropyl Betaine | 1.00 |
| Tween 20-LQ-(RB) | Polysorbate-20 | 2.00 |
| Phenoxyethanol | Phenoxyethanol | Qs |
| Fragrance | Fragrance | 0.10 |
| Phase C | | |
| Ingredient of the invention | | 3.00 |

Procedure: Weigh and put phase A under gentle propeller stirring. Weigh and homogenize phase B. Add phase B into phase A under rapid propeller stirring. Add phase C into phase A+B under gentle propeller stirring. Add phase D under gentle propeller stirring.

Example of additional ingredients that can be added to this formulation:

Birch SAP™: Skin toning and moisturizing ingredient marketed by Sederma, based on raw sap from birch sapwood. 3% can be added at the end of the formulation.

EXAMPLE 17

Patch for Eye Contour (for Treatment of Dark Circles and Under Eye Bags)

| Ingredients | INCI names | Weight % |
|---|---|---|
| Phase A | | |
| H₂O | Water | Qsp 100 |
| Potassium sorbate | Potassium Sorbate | 0.10 |
| Phase B | | |
| Glycerin | Glycerin | 3.00 |
| Phenoxyethanol | Phenoxyethanol | qs |
| Satiagel VPC 614 | *Chondrus Crispus* (Carrageenan) Extract | 1.00 |
| Viscogum BCR 13/250 | Locust Bean Gum & Sucrose | 1.00 |
| Phase C | | |
| H₂O | Water | 5.00 |
| NaOH 30% | Potassium Hydroxide | 0.50 |
| Phase D | | |
| Ingredient according to the invention | | 3.00 |

| Ingredients | INCI names | Weight % |
|---|---|---|
| Phase E | | |
| Fragrance | Fragrance | 0.10 |

Procedure: Weigh phase A and put it under propeller stirring in a water bath at 85° C. Weigh and homogenize phase B. Add phase B into phase A under propeller stirring propeller. Leave it for homogenization for 1 hour under blade stirring. Out of the water bath, let cool under blade stirring. Add phase C, below 70° C. Add phase D. Add phase E. Pour the patches in the mold and let cool for 2 hours at room temperature.

Example of additional ingredients that can be added to this formulation:

Wonderlight™: lightening agent marketed by Sederma. 3% can be added before phase C to the formulation before cooling.

EXAMPLE 18

Fluid Gel Form

| Ingredients | INCI names | Weight % |
|---|---|---|
| Phase A | | |
| H$_2$O | Water | Qsp 100 |
| Potassium sorbate | Potassium Sorbate | 0.10 |
| Phase B | | |
| Renex G26 | Glycereth-26 | 5.00 |
| Phenoxyethanol | Phenoxyethanol | Qs |
| Crovol A70 | PEG-60 Almond Glycerides | 0.50 |
| N-Hance HP40 | Hydroxypropyl Guar | 0.40 |
| Keltrol CG-SFT | Xanthan Gum | 0.50 |
| Phase C | | |
| Tween 20 | Polysorbate-20 | 1.00 |
| Fragrance | Fragrance | 0.10 |
| Phase D | | |
| Ingredient according to the invention | | 3.00 |

Procedure: Weigh phase A and put it under propeller stirring. Weigh and homogenize phase B. Add phase B into phase A under propeller stirring propeller. Mix well. Weigh phase C and homogenize. Add phase C into phase A+B under propeller stirring. Mix well. Add phase D in the previous phase, mix well.

Example of additional ingredients that can be added to this formulation:

Skin Tightener™: ingredient marketed by Sederma, an association of prolamines with polymannuronate that tightens and smoothes skin. 10% can be added at the end of the formulation.

G) In Vivo Evaluations of the Glycation Activity of the *Albizia Julibrissin* Extract The activity on glycation according to the invention of the *Albizia Julibrissin* extract has been shown in in vivo tests given below.

A cream prepared according to Example 1 was used for these tests.

Principle

The efficacy tests were performed on a panel of 24 volunteers presenting visible signs of stress (fatigue signs) on their face or a net advanced glycation cutaneous level.

In addition, on a panel of 14 volunteers, the amount of advanced glycation end products (AGEs) was evaluated by measurements in adhesive strippings A second panel of 20 volunteers with the same characteristics, it has been sought to improve this condition.

Several complementary methods were used in this study:

An analysis of advanced glycation end-product content by in vivo measurement of their auto-fluorescence using the AGE-Reader™ device recited thereafter.

Measurement of AGE content in adhesive strippings taken from the forearm (ex vivo method).

A skin fatigue and slackening analysis using the Reviscometer®

A self-completed quasi-daily and weekly assessment of facial fatigue recorded by the volunteer on waking.

Protocol

Specific Study Inclusion Criteria

Women in the "stressed" skin study were selected on the objective basis of age—they had to be between 50 and 70 years old—and from AGE-Reader™ measurements showing sufficiently high levels of glycation products.

For the fatigue signs and adhesive strip samples, the volunteers had to have facial signs of fatigue (dark circles, drawn facial features, dull complexion) and skin showing excessive forearm slackening.

The volunteers had to be active people reporting that they did not have enough time to rest. They had to follow a wash-out period of 15 days (using only the placebo).

Furthermore, all 3 tests required the volunteers to remain in a constant hormonal state during the 3 months before the test and during the test (no change in contraception or in substitution or curative treatment).

They had to use only the cosmetics provided during the study.

Type of Study and Duration

The studies were conducted single-blind with non-invasive measurements on:

24 volunteers with stressed skin (average age 60 years old [range 53 to 69 years old]) who applied a day cream and night cream according to the invention to their dominant forearm. The placebo cream was applied to the contralateral arm.

14 volunteers with signs of fatigue (average age 43.5 years old [range 38 to 50 years old]) who applied a day cream and a night cream according to the invention respectively to one of their forearms. The placebo cream was applied to the contralateral arm.

20 volunteers with signs of fatigue (average age 43 years old [range 31 to 50 years old]) who applied a day cream and a night cream according to the invention respectively to their face and one forearm.

The day and night creams according to the invention were applied by massaging once daily for 2 months and the placebo cream was applied twice daily.

The study is summarised in the diagram below.

| T0 | T 1 month | | T 2 months |
|---|---|---|---|
| AGE-Reader™ | | | AGE-Reader™ |
| Adhesives | | | Adhesives |
| Reviscometer® | Reviscometer® | | Reviscometer® |
| Self-assessment | Self-assessment | Self-assessment | Self-assessment |

Statistical studies were performed using the Student t test or a Wilcoxon non-parametric test if necessary. Two-tailed tests for paired series were used in each case.

Tolerability

The clinical study was carried out under medical supervision and showed that the product was tolerated extremely well by the volunteers.

1. Analysis of Advanced Glycation End Product Content Using the AGE-Reader™ Principle The AGE-Reader™ (DiagnOptics Technologies) is the first medical device allowing non-invasive measurement of AGEs accumulation. The volunteer's skin is exposed to light at a wavelength of 370±50 nm which excites functional fluorescent groups, particularly those in the AGEs. The reflected light is transmitted selectively by a 50 μm diameter fibre and measured by spectrophotometry. A correlation between volunteer skin autofluorescence and their different AGE content can be determined thanks to this device.

In practice, the volunteer places his/her forearm on the instrument and measurements are taken through a 1 cm$^2$ window Results

TABLE 16

Change in the glycation product content measured by AF* with the AGE-Reader ™, following application of the creams of the invention or the placebo cream.

| | Creams according to the invention | Placebo |
|---|---|---|
| | 2.44 +/− 0.36 | 2.67 +/− 0.55 |
| Change | −0.224 | |
| Change % | −8.6% | |
| [max] found | →[−33%] | |
| Significance | p < 0.05 | |
| Responders vs. placebo (%) | 71% | |

*AF = Arbitrary auto-fluorescence units, 24 volunteers, n = 3 measurements

The results show that after applications of the day cream then the night cream daily for 2 months, a significant difference in auto-fluorescence was found compared to the placebo.

This fall is of −8.6% reflects the fall in glycation end-product content. Very satisfactorily, a high proportion of volunteers responded (71%).

2. Study on AGEs in Adhesive Strippings (Ex Vivo Study)

Principe

A test on volunteers with visible signs of skin fatigue (N=14) was used to confirm the fall in AGEs, seen with the AGE-Reader™, on cultured cells and in explants (see in vitro section) treated with an extract of *Albizia Julibrissin* according to the invention.

AGE content was measured on adhesive strippings taken before and after application of a day and night cream according to the invention, respectively, to the forearm for two months.

The adhesive strippings were removed and stored at −80° C. Proteins in the strippings were extracted into a buffer and the homogenates were then loaded onto a polyacrylamide gel to run the proteins and transfer them onto a nitrocellulose membrane for development by Western Blot. The anti-AGE antibodies already described in the in vitro section were used again. The blots were developed by chemiluminescence on the major bands of approximately 60 kDa representing the keratins. Total protein was measured in parallel to standardise results.

Results

TABLE 17

Change in the AGE protein content (keratins) after applying the creams according to the invention (N = 14 volunteers).

| | According to the invention | | Placebo | |
|---|---|---|---|---|
| | T0 | T 2 m | T0 | T 2 m |
| Mean | 58.8 ± 16.3 | 64.5 ± 22.7 | 59.4 ± 17.6 | 81.1 ± 33.2 |
| % change vs. T0 (significance) | | +9.7% (dns) | | +36.7% (p > 0.01) |
| Change (Invention-Placebo) (significance) | | −27.0% (p < 0.05) | | |

The results showed that AGEs increased between T0 and T2 months and that this increase was 27% less thanks to the use of the creams according to the present invention comprising the *Albizia Julibrissin* extract.

3. Analysis of Skin Fatigue and Slackening with the Reviscometer® Principe

The RV 600 Reviscometer® (Courage & Khazaka) measures the acoustic wave propagation time in skin after the wave has been emitted from its surface: this index is known as the Resonance Running Time (or RRT). The instrument's skin probe consists of an acoustic emitter 2 mm distant from the receiver. As the wave does not pass more than 0.5 mm into the skin it allows the qualities of the dermis to be examined. Sound propagation speed in a material depends on the density and tension of the material. Acoustic waves preferentially follow "wires" formed by the fibres of the dermis. The condition of these fibres therefore directly influences wave propagation.

By gradually rotating the probe around its axis, the different propagation times can be mapped. Skin which is tired has less dense, less taut fibres, thereby increasing the propagation time. Furthermore fatigued skin with poor tone also has creases with preferential directions (skin anisotropism). This changes the propagation time along some measurement axes.

Several parameters obtained with the Reviscometer® RV 600 describe the characteristics of the skin state. From these parameters, the following parameters were used:

The maximum resonance running time (or RRTmax) which reflects reflecting the "slowness" of sound in the skin, which reflects the cutaneous fatigue.

The RRTmax/RRTmin ratio, which demonstrates the anisotropic nature of the skin, the magnitude of the ratio reflecting "slackening" of the skin which is not homogeneous in all directions.

Results

TABLE 18

Change in the slowness (cutaneous fatigue) and slackening after applications of the creams according to the invention

|  | Slowness — cutaneous fatigue (RRTmax) | | | Slackening (RRTmax/RRT min) | | |
| --- | --- | --- | --- | --- | --- | --- |
|  | T0 | T 1 month | T 2 months | T0 | T 1 month | T 2 months |
|  | 842.0 ± 677.3 | 620.5 ± 508.8 | 583.4 ± 446.7 | 10.08 ± 9.6 | 6.03 ± 4.2 | 5.6 ± 4.5 |
| % change vs. T0 |  | −26.3% | −30.7% |  | −40.2% | −44% |
| Significance |  | p < 0.05 | p < 0.05 |  | p < 0.01 | p < 0.01 |
| Maximum |  | → −63% | → −69% |  | → −65% | → −81% |
| Responders |  | 80% | 80% |  | 80% | 85% |

20 volunteers, n = 3 repetitions

The results show that application of the creams according to the invention reduced slowness of sound propagation in the volunteers by 26.3% from the $1^{st}$ month by 30.7% from the $2^{nd}$ month.

In parallel, slackening, measured from the RRTmax/RRTmin ratio, fell from T 1 month by 40.2% compared to T0; an improvement was found after 2 months (−44%).

After applying the creams according to the invention, the skin thus recovers its vitality, as demonstrated by the reduction in slowness and slackening. These results with the Reviscometer® show that the creams comprising the *Albizia Julibrissin* extract according to the invention markedly improved the density and homogeneity of dermal fibres.

4. Self-Assessment of Facial Fatigue

Principle

In order to obtain information about the "raw" state of facial fatigue, each volunteer assessed different criteria for fatigue in a real-life situation after waking up, in front of a mirror. The various fatigue criteria and study design are shown in the diagram below.

| Every 2 days: | General facial fatigue | | | |
| --- | --- | --- | --- | --- |
| Every week: | More specific observations of: | | | |
|  | Dark circles/Under eye bags/Drawn facial features/ Dull complexion | | | |
|  | 0 (none) | 1 (mild) | 2 (moderate) | 3 (pronounced) |

Results a. General Fatigue

As shown in FIG. 1, Table 19 represents the reduction in facial fatigue during applications of the cream according to the invention (20 volunteers).

Self-assessments by the volunteers, every two days, of their general facial fatigue revealed a constant regular fall in general fatigue throughout the application of the cream according to the invention.

The average score for the 20 volunteers fell from 2.05 (representing moderate facial fatigue) to 1.15 (representing mild facial fatigue).

This demonstrates that the impression of general fatigue fell by 36% at T 1 month and by 50% after 2 months. The fall became unequivocally significant (p<0.01) from day 10.

b. Specific Indices

Volunteers also added more details in a questionnaire about under eye bags, dark circles, drawn facial features and dull complexion.

The results of the weekly self-assessments completed by the volunteers fully confirm the important fall in the impression of general facial fatigue. The overall intensity of the four indices examined fell from T1 month and a pronounced additional fall was seen at T 2 months.

Figure 2:
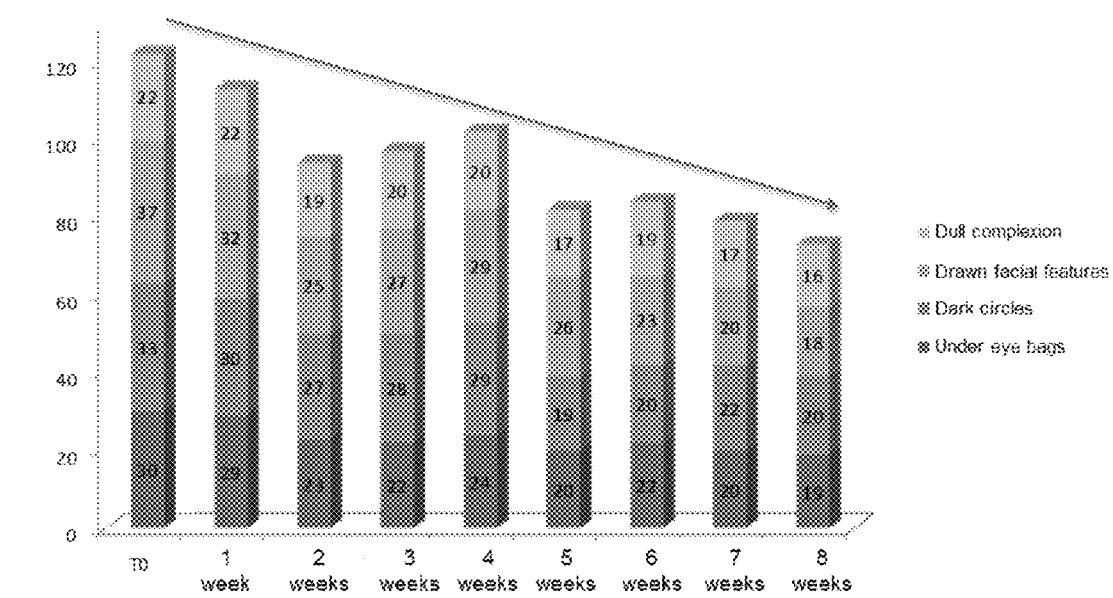
FIG. 2 is a bar graph that represents an aspect of the present invention.

As shown in FIG. 2, Table 20 represents the reduction in signs of facial fatigue in the morning, with use of the creams of the invention (20 volunteers).

The "under eye bags" index fell from a score of 30 to a score of 24 (T1 month, −20%) and then to 19 (T2 months, −37%).

The "dark circles" index fell from a score of 33 to a score of 29 (T1 month, −12%) and then to 20 (T2 months, −40%).

The "drawn facial features" index fell from a score of 37 to a score of 29 (T1 month, −22%) and then to 18 (T2 months, −51%).

The "dull complexion" index fell from a score of 22 to a score of 16 (T2 months, −27%).

After 2 months of treatment, the volunteers reported their objective signs of fatigue to be mild or non-existent.

H) In Vivo Evaluations of the Glycation Activity of the Combination of the *Albizia Julibrissin* Extract and Darutoside Three independent clinical tests were performed to demonstrate the action of the product on:

1. Wrinkles and eyelids
2. Dark circles
3. Eye look

The cream of example 13 of paragraph F) was used for these tests.

1. Test on Wrinkles and Eyelids

Principle

The aim of the study was to demonstrate a reduction in wrinkles and a smoothing of eyelid fold after a twice daily application for 56 days.

The study was conducted on a panel of 22 Caucasian women of mean age of 60 years (40-79) with wrinkles in the crow's feet. The study was in conducted in single-blind versus placebo. Volunteers applied the cream according to the invention on the eye contour, twice daily for 56 days. The placebo cream was applied contralaterally.

Different methods were associated with each time of the study (T0, T56j)

SiMo™ Fingerprints for quantification of crow's feet wrinkles

FOITS technique for quantification of the eyelid fold.

Photo bench for the quantification of crow's feet wrinkles and eyelid fold by an expert team.

Results a. Silflo™ Fingerprints for Quantification of Crow's Feet Wrinkles

At each measurement time, a negative cast of the skin is made with a Silflo™ silicone polymer on the selected sites (crow's feet wrinkles). Each cast is then scanned by the technique of drop shadows through a Quantirides Station™ (Monaderm). Briefly, the negative cast of crow's feet wrinkles is illuminated by a tangential light (LED lamp; 35°). It generates drop shadows behind every wrinkle The image acquisition is performed using a high resolution digital camera (1920×1440 pixels). Images are recorded in 256 gray levels and then analyzed by a specific Mountains Map™ software to quantify reliefs.

TABLE 21

| | Product | | | | | | Placebo | | | | | |
|---|---|---|---|---|---|---|---|---|---|---|---|---|
| | Volume of the main wrinkle (mm³) | | Depht of the main wrinkle (μm) | | Opening angle of wrinkles (°) | | Volume of the main wrinkle (mm³) | | Depht of the main wrinkle (μm) | | Opening angle of wrinkles (°) | |
| 22 volonteers | T0 | T2 m | T0 | T2 m | T0 | T2 m | T0 | T2 m | T0 | T2 m | T0 | T2 m |
| Mean | 0.71 | 0.61 | 105.8 | 95.8 | 83.3 | 92.6 | 0.70 | 0.67 | 105.4 | 104.0 | 90.4 | 90.4 |
| Standard deviation | 0.20 | 0.18 | 15.7 | 16.6 | 19.6 | 19.5 | 0.18 | 0.18 | 13.9 | 12.2 | 18.6 | 16.3 |
| Var %/T0 | | −14.1% | | −9.5% | | 11.2% | x | −4.3% | x | −1.3% | x | 0% |
| Student t test, p = | | 0.001 | | 0.001 | | 0.003 | x | 0.221 | x | 0.471 | | 0.990 |
| Student t test, p = | | 0.044 | | 0.014 | | 0.027 | | | | | | |

After 2 months of application of the cream according to the invention, a highly significant improvement ($p<0.01$) of the volume (−14%), of the mean depth (−9.5%) as well as the wrinkle opening (+11.2%) is noted. These improvements are also significantly different ($p<0.05$) from the little changes occurred with the placebo cream.

b. FOITS Technique for Quantification of the Eyelid Fold

Principle

The FOITS (Fast Optical In vivo Topometry System) is based on the analysis of the fringe projection on the study area, here the eyelids. The used device, a Dermatop™ (EOTech) comprises a projector and a camera. These two instruments are integral and form a specific angle, for triangulation. The study of the deformation fringes by the relief of the zone allows a 3D reconstruction of the relief. 3D Moutains Map™ software of acquisition analysis is then used to extract a profile of the eyelid fold. The height of the fold as well as its surface was calculated.

Results

TABLE 22

| | Product | | | | | Placebo | | | |
|---|---|---|---|---|---|---|---|---|---|
| | height of the eyelid fold (mm) | | Falling surface (mm2) | | | height of the eyelid fold (mm) | | Falling surface (mm2) | |
| 18 volonteers | T0 | T2 m | T0 | T2 m | 18 volonteers | T0 | T2 m | T0 | T2 m |
| Mean | 0.756 | 0.602 | 1.016 | 0.880 | Mean | 0.700 | 0.693 | 0.920 | 0.921 |
| Standard deviation | 0.348 | 0.333 | 0.589 | 0.532 | Standard deviation | 0.354 | 0.365 | 0.476 | 0.519 |
| Var % / T0 | x | −20.4% | X | −13.3% | Var %/T0 | x | −1% | x | 0.1% |
| Student t test vs. T0, p = | x | 0.003 | X | 0.044 | Student t test, p = | x | 0.863 | x | 0.987 |
| Student t test vs. placebo, p = | x | 0.036 | X | 0.161 | | | | | |

After 2 months of application of the cream according to the invention, a significant decrease in the height of the fold of 20% (p<0.01) is noted. This decrease was also significantly different (p<0.05) from the almost null decrease of −1% observed on the site receiving placebo.

Regarding the falling surface, after application 2 months of the cream of the invention, there is a significant decrease of 13% (p<0.05). On the Placebo side, there is no change. The difference between product and placebo was not significant but the trend is with p=0.16.

c. Photo Bench for the Quantification of Crow's Feet Wrinkles and Eyelid Fold by an Expert Team
Principle The standardized photos were realized by a photographic bench HeadScan™ (Orion concept) consisting of a high-definition Nikon D70 digital camera, a specific lighting and a restraint system for volunteers. Voluntary posture, the photo and lighting settings were standardized and controlled to be reproduced over time. For this evaluation, the photos were made in diffuse light to properly see colors and relief and have a result as close as possible to reality.

The area around the eyes (eye contour) taken at T0 and T56j was jointly presented to six experts who were asked to say whether they agree, disagree, or neither agree nor disagree with the following statements:
1. The eyelid fold is less pronounced
2. The skin appears smooth (fine lines and wrinkles are reduced)

Results
The results to the question "The fold is less marked, the skin is smoother?" demonstrate that 47% of the replies show a favorable action of the product vs. 10.5% a defavorable action (p<01). Furthermore, the comparison with the placebo demonstrates that these 47% of favorable replies are significantly superior to the 28% of favorable replies obtained with the application of the placebo.

The results to the question "The skin seems smoother (wrinkles and fine lines are diminished)?" demonstrate that 49% of the replies show a favorable action of the product vs. only 4% a defavorable action (p<01). Furthermore, the comparison with the placebo demonstrates that these 49% of favorable replies are significantly superior to the 30% of favorable replies obtained with the application of the placebo.

2. Test on Dark Circles
Principle

The aim of the study was to demonstrate a diminishing of dark circles after a twice daily application for 28 days and 56 days.

The study was conducted on a panel of 24 Caucasian women of mean age of 18 years with dark circles under the eyes. The study was in conducted in single-blind versus placebo. Volunteers applied the cream according to the invention on the eye contour, twice daily for 28 days and 56 days. The placebo cream was applied contralaterally.

A photo bench was used to obtain standardized photos for the different times of measurement of the study (T0, T28d and T56d). The color of the dark circles was then analyzed.

Standardized photographs were obtained with a photographic system consisting of a flash lighting system (R1C1 Nikon™) of a professional camera (D300 Nikon™) equipped with a macro lens (AF-S Micro Nikkor™ 60 mm).

When measuring dark circles, it is considered that the accumulation of hemoglobin in the area of the eye contour produces a color change. This variation is associated with variation of the red component and blue component of the color of the skin (the purple color is characteristic of the rings).

An image analysis software capable of working in the reference space CIELab™ was then used. The CIELab colorimetric space defines a color by 3 coordinates:
L*: from 0 (black) to 100 (white)
a*: from 100 (red) to −100 (green)
b*: from 100 (yellow) to −100 (blue).

In the present situation, the reducing of the +a* and the −b* were expected.

The evaluation of the color of the circles is done by defining the area of circles and comparing it to an area close (temples in our case). A Δa for the red component and a Δ-b for the blue component are thus determined.

Results

TABLE 23

|  | Invention cream | | | Placebo cream | | |
| --- | --- | --- | --- | --- | --- | --- |
| Δa = red | t0 | T30 | T60 | t0 | T30 | T60 |
| mean | 9.38 | 8.93 | 8.69 | 9.34 | 9.38 | 9.59 |
| % change vs. T0 |  | −4.5% | −7.5% |  | 0.8% | 3% |
| T student vs. T0 |  | 0.072 | 0.037 |  | 0.812 | 0.290 |
| T student invention cream vs. placebo |  | 0.042 | 0.009 |  |  |  |

After 30 days of application of the cream of the invention, a decrease of the red component of 4.5% compared to an increase of +0.8% for placebo-treated side is noted. The difference of the action between the cream of the invention and the placebo is significant with p<0.05.

After 60 days, the effect of the cream of the invention is increased with a significant decrease up to 7.5% (p<0.05), whereas the side treated with placebo cream showed a deterioration of 3%. The difference of the effect between the cream of the invention and the placebo cream is very significant with p<0.01.

TABLE 24

|  | Cream of the invention | | | Placebo cream | | |
| --- | --- | --- | --- | --- | --- | --- |
| Δ − b = blue | t0 | T30 | T60 | t0 | T30 | T60 |
| Mean | −5.86 | −5.68 | −5.42 | −5.73 | −5.77 | −5.89 |
| % change vs. T0 |  | 3.2% | 8.2% |  | −1.9% | −4.1% |
| T student vs. T0 |  | 0.134 | 0.020 |  | 0.766 | 0.399 |
| T student invention cream vs. placebo |  | 0.246 | 0.022 |  |  |  |

There is 30 days after application of the cream of the invention a decrease of the blue component of 3.2% compared to an increase of 1.9% in the placebo-treated side.

After 60 days, the effect of the product allows a significant reduction of the blue component of 8.2% (p<0.05), whereas the side treated with placebo showed a deterioration of 4.1%. The effect difference between product and placebo is significant with p<0.05.

3. Test on the Action on Eye Look

Principle: The study of the efficacy of the cream of the invention was to demonstrate improvement perceived by the volunteer at their eye look (overall fatigue, dark circles, eye bags, fine lines). The evaluation was performed every 2-3 days for an application twice daily for 28 days.

The study was conducted on a panel of 105 Caucasian women of average age 51 years (between 40 and 60 years), claiming to have a tired look and presenting one of the 2 to 3 following characteristics: fine lines around the eyes, under eye bags, dark circles. Volunteers applied the cream according to the invention on the eye contour twice daily for 28 days.

The evaluation was performed in the morning before the first application of the day, by a self-assessment questionnaire.

4 questions were asked to the volunteers:
1. How do you rate the fatigue of your eyes on getting up? (Global)
2. How do you rate the importance of the presence of fine lines?
3. How do you rate the importance of under eye bags?
4. How do you rate the importance of dark circles?

Responses (score) were: none (0), mild (1), moderate (2), important (3).

Question 1 was asked every Monday, Wednesday and Friday (13 evaluations on 28 days), whereas questions 2, 3 and 4 only once per week (5 evaluations on 28 days).

TABLE 25

Mean evaluation of the characteristics of the eye look by the global population.

| | Global | Dark circles | Under eye bags | Fine lines |
|---|---|---|---|---|
| D0 | 2.28 | 2.04 | 1.95 | 2.15 |
| D2 | 2.07 | / | / | / |
| D4 | 1.90 | / | / | / |
| D7 | 1.78 | 1.58 | 1.64 | 1.82 |
| (decrease % D7/D0) | 16% | 22% | 16% | 16% |
| D9 | 1.73 | / | / | / |
| D11 | 1.70 | / | / | / |
| D14 | 1.57 | 1.47 | 1.41 | 1.65 |
| (decrease % D14/D7) | 9% | 6% | 12% | 8% |
| D16 | 1.54 | / | / | / |
| D18 | 1.52 | / | / | / |
| D21 | 1.43 | 1.27 | 1.27 | 1.38 |
| (decrease % D14/D7) | 4% | 10% | 7% | 12% |
| D23 | 1.38 | / | / | / |
| D25 | 1.32 | / | / | / |
| D28 | 1.27 | 1.11 | 1.14 | 1.23 |
| (decrease % D28/D21) | 7% | 7% | 6% | 7% |
| (decrease % D28/D0) | 44% | 46% | 42% | 43% |

The results are expressed as mean scores. The decrease in the average value of items for days 7, 14, 21, 28 is expressed as % of change. The statistical tests are t Student test.

From the analysis of the above result table it can be said:
The cream of the invention improves on getting up the fatigue of the eye look and dark circles, eye bags and fine lines. At the end of the 28 uses, participants evaluated an average of 42% to 46% reduction on the 4 listed items. The decrease was statistically significant with p<0.01.

Comparison of the fatigue of the eye look with the appearance of eye look at D0, shows a significant decrease from 2 days of application (−9%, p<0.01, 2.7 score versus 2.28), which reached −16% at D7.

The comparison of the appearance of dark circles, bags and fine lines with the appearance at D0, shows a significant decrease after 7 days of application (16% for fine lines and bags, p<0.01, −22% for dark circles, p<0.01).

The invention claimed is:

1. A composition for the treatment of glycation of skin proteins to obtain a synergistic effect in a system comprising:
   an extract of *Albizia Julibrissin* in the amount of about 0.001% to about 10% by weight of the composition and Darutoside in the amount of about 0.001% to about 10% by weight of the composition; and
   a physiologically acceptable medium.

2. The composition according to claim 1, wherein said *Albizia Julibrissin* extract is an extract of flowers and/or seeds.

3. The composition according to claim 1, wherein the Darutoside is extracted from *Siegesbeckia Orientalis*.

4. The composition according to claim 1, wherein said composition further comprises one or more additional active ingredients selected from the group consisting of lightening agents, anti-redness agents, anti-spot agents, skin calming agents, agents for the treatment of sensitive or reactive skin, UV sunscreens, moisturizing agents, humectants, exfoliating agents, smoothing agents, toning agents, anti-aging agents, anti-wrinkle agents, agents for improving the mechanical and elastic properties of skin, agents for improving skin radiance, detoxifying agents, anti-hair regrowth agents, agents acting on the skin barrier, anti-acne agents, agents acting on the secretion of sebum, matting agents, unifying agents, anti-inflammatory agents, anti-oxidants, anti-radicals, anti-glycants, agents for reducing fatigue of eye contour, agents for reducing fine lines and wrinkles around the eyes and on eyelids, agents for reducing under eye bags and dark circles, agents for promoting blood circulation, peptides, and vitamins.

5. The composition according to claim 1, wherein the synergistic effect is a decrease in elastin non-enzymatic glycation.

6. A method for cosmetically treating skin comprising topically applying an effective amount of the composition according to claim 1 to a subject in need thereof.

7. The method according to claim 6 wherein said cosmetic treatment reduces cutaneous fatigue in said subject.

8. The method according to claim 6 wherein said cosmetic treatment is cosmetic treatment of eye contour in said subject.

9. The method according to claim 8 wherein the cosmetic treatment of eye contour is the cosmetic treatment of dark circles and under eye bags in the subject.

* * * * *